US010683390B2

(12) United States Patent
Farmer et al.

(10) Patent No.: US 10,683,390 B2
(45) Date of Patent: Jun. 16, 2020

(54) SYSTEMS AND PROCESSES FOR POLYMER PRODUCTION

(71) Applicant: Novomer, Inc., Boston, MA (US)

(72) Inventors: Jay J. Farmer, Boston, MA (US);
Peter Galebach, Madison, WI (US);
Kyle Sherry, Rochester, NY (US);
Sadesh H. Sookraj, Cambridge, MA (US)

(73) Assignee: Novomer, Inc., Rochester, NY (US)

( * ) Notice: Subject to any disclaimer, the term of this patent is extended or adjusted under 35 U.S.C. 154(b) by 46 days.

(21) Appl. No.: 15/550,161

(22) PCT Filed: Feb. 12, 2016

(86) PCT No.: PCT/US2016/017797
§ 371 (c)(1),
(2) Date: Aug. 10, 2017

(87) PCT Pub. No.: WO2016/130947
PCT Pub. Date: Aug. 18, 2016

(65) Prior Publication Data
US 2018/0094100 A1 Apr. 5, 2018

Related U.S. Application Data

(60) Provisional application No. 62/116,238, filed on Feb. 13, 2015.

(51) Int. Cl.
*C07C 51/09* (2006.01)
*C08G 63/08* (2006.01)
*C08F 120/06* (2006.01)
*C07C 57/04* (2006.01)
*C08F 4/30* (2006.01)
*C08F 122/02* (2006.01)

(52) U.S. Cl.
CPC .............. *C08G 63/08* (2013.01); *C07C 51/09* (2013.01); *C07C 57/04* (2013.01); *C08F 4/30* (2013.01); *C08F 120/06* (2013.01); *C08G 2650/04* (2013.01)

(58) Field of Classification Search
CPC ................................ G06Q 30/02; C08G 63/08
USPC ........................................................ 528/355
See application file for complete search history.

(56) References Cited

U.S. PATENT DOCUMENTS

| | | | |
|---|---|---|---|
| 2,526,554 A | 10/1950 | Gresham et al. |
| 6,852,865 B2 | 2/2005 | Coates et al. |
| 8,445,703 B2 | 5/2013 | Allen et al. |
| 8,796,475 B2 | 8/2014 | Allen et al. |
| 9,096,510 B2 | 8/2015 | Porcelli et al. |
| 9,156,803 B2 | 10/2015 | Allen et al. |
| 9,206,144 B2 | 12/2015 | Allen et al. |
| 9,327,280 B2 | 5/2016 | Lee et al. |
| 9,403,788 B2 | 8/2016 | Lee et al. |
| 9,493,391 B2 | 11/2016 | Allen et al. |
| 9,738,784 B2 | 8/2017 | Allen et al. |
| 9,914,689 B2 | 3/2018 | Porcelli et al. |
| 10,065,914 B1 | 9/2018 | Ruhl et al. |
| 10,099,988 B2 | 10/2018 | Farmer et al. |
| 10,099,989 B2 | 10/2018 | Sookraj |
| 10,144,802 B2 | 12/2018 | Sookraj |
| 10,221,150 B2 | 3/2019 | Farmer et al. |
| 10,221,278 B2 | 3/2019 | Lee et al. |
| 10,245,559 B2 | 4/2019 | Lapointe et al. |
| 10,428,165 B2 | 10/2019 | Sookraj |
| 10,457,624 B2 | 10/2019 | Sookraj et al. |
| 10,479,861 B2 | 11/2019 | Lee et al. |
| 2012/0123137 A1 | 5/2012 | Allen et al. |
| 2013/0165670 A1 | 6/2013 | Allen et al. |
| 2013/0209775 A1 | 8/2013 | Allen et al. |
| 2013/0281715 A1 | 10/2013 | Allen et al. |
| 2014/0018570 A1 | 1/2014 | Pazicky et al. |
| 2014/0018574 A1 | 1/2014 | Raith et al. |
| 2014/0275575 A1 | 9/2014 | Allen et al. |
| 2014/0296522 A1 | 10/2014 | Lee et al. |
| 2014/0309399 A1 | 10/2014 | Porcelli et al. |
| 2015/0005513 A1 | 1/2015 | Lee et al. |

(Continued)

FOREIGN PATENT DOCUMENTS

| | | |
|---|---|---|
| JP | 2015-509497 A | 3/2015 |
| JP | 2015-522595 A | 8/2015 |

(Continued)

OTHER PUBLICATIONS

International Search Report and Written Opinion received for PCT Patent Application No. PCT/US2016/017797, dated May 5, 2016, 9 pages.

(Continued)

*Primary Examiner* — Duc Truong
(74) *Attorney, Agent, or Firm* — Young Basile Hanlon & MacFarlane, P.C.

(57) ABSTRACT

Disclosed are compositions, systems and methods related to a polypropiolactone composition comprising polypropiolactone polymers. Such polymers include polypropiolactone chains of Formula (I): [Formula should be inserted here] where n is an integer from 10 to about 1,000 and Y is either —H or a cation.

15 Claims, No Drawings

(56) References Cited

U.S. PATENT DOCUMENTS

| | | |
|---|---|---|
| 2015/0141693 A1 | 5/2015 | Allen et al. |
| 2015/0299083 A1 | 10/2015 | Porcelli et al. |
| 2015/0368394 A1 | 12/2015 | Allen |
| 2016/0016876 A1 | 1/2016 | Mahoney |
| 2016/0102040 A1 | 4/2016 | Allen et al. |
| 2016/0102068 A1 | 4/2016 | Allen et al. |
| 2016/0288057 A1 | 10/2016 | Lapointe et al. |
| 2017/0001946 A1 | 1/2017 | Sookraj |
| 2017/0002136 A1 | 1/2017 | Sookraj |
| 2017/0029352 A1 | 2/2017 | Sookraj et al. |
| 2017/0073463 A1 | 3/2017 | Lee et al. |
| 2017/0080409 A1 | 3/2017 | Farmer et al. |
| 2017/0096407 A1 | 4/2017 | Sookraj |
| 2017/0107103 A1 | 4/2017 | Sookraj et al. |
| 2017/0145126 A1 | 5/2017 | Mahoney |
| 2017/0225157 A1 | 8/2017 | Lee |
| 2017/0247309 A1 | 8/2017 | Porcelli et al. |
| 2017/0267618 A1 | 9/2017 | Sookraj et al. |
| 2018/0016219 A1 | 1/2018 | Farmer et al. |
| 2018/0022677 A1 | 1/2018 | Sookraj |
| 2018/0029005 A1 | 2/2018 | Sookraj |
| 2018/0030014 A1 | 2/2018 | Sookraj et al. |
| 2018/0030015 A1 | 2/2018 | Farmer et al. |
| 2018/0030201 A1 | 2/2018 | Farmer et al. |
| 2018/0057619 A1 | 3/2018 | Sookraj |
| 2018/0153746 A1 | 6/2018 | Sookraj |
| 2018/0155490 A1 | 6/2018 | Sookraj |
| 2018/0155491 A1 | 6/2018 | Sookraj |
| 2018/0282251 A1 | 10/2018 | Sookraj |
| 2018/0305286 A1 | 10/2018 | Sookraj |
| 2018/0305289 A1 | 10/2018 | Sookraj et al. |
| 2018/0354881 A1 | 12/2018 | Farmer et al. |
| 2018/0354882 A1 | 12/2018 | Sookraj |
| 2019/0002293 A1 | 1/2019 | Sookraj et al. |
| 2019/0002385 A1 | 1/2019 | Sookraj |
| 2019/0002400 A1 | 1/2019 | Sookraj |
| 2019/0030520 A1 | 1/2019 | Lee |
| 2019/0031592 A1 | 1/2019 | Sookraj et al. |
| 2019/0047972 A1 | 2/2019 | Sookraj |
| 2019/0071388 A1 | 3/2019 | Sookraj |
| 2019/0071538 A1 | 3/2019 | Sookraj |
| 2019/0076834 A1 | 3/2019 | Sookraj |
| 2019/0076835 A1 | 3/2019 | Sookraj |
| 2019/0106532 A1 | 4/2019 | Sookraj |
| 2019/0106533 A1 | 4/2019 | Sookraj |
| 2019/0255488 A1 | 8/2019 | Lapointe et al. |
| 2019/0255512 A1 | 8/2019 | Lee et al. |
| 2019/0256650 A1 | 8/2019 | Lee et al. |
| 2019/0315702 A1 | 10/2019 | Sookraj et al. |
| 2019/0345125 A1 | 11/2019 | Farmer et al. |
| 2019/0359581 A1 | 11/2019 | Pokrovski et al. |

FOREIGN PATENT DOCUMENTS

| | | |
|---|---|---|
| JP | 2015-529644 A | 10/2015 |
| WO | 2004/089923 A1 | 10/2004 |
| WO | 2010/118128 A1 | 10/2010 |
| WO | 2012/030619 A1 | 3/2012 |
| WO | 2012/051219 A2 | 4/2012 |
| WO | 2012/158573 A1 | 11/2012 |
| WO | 2013/063191 A1 | 5/2013 |
| WO | 2013/122905 A1 | 8/2013 |
| WO | 2013/126375 A1 | 8/2013 |
| WO | 2014/004858 A1 | 1/2014 |
| WO | 2014/008232 A2 | 1/2014 |
| WO | 2014/012855 A1 | 1/2014 |
| WO | 2015/085295 A2 | 6/2015 |
| WO | 2015/138975 A1 | 9/2015 |
| WO | 2015/171372 A1 | 11/2015 |
| WO | 2015/184289 A1 | 12/2015 |
| WO | 2016/015019 A1 | 1/2016 |
| WO | 2016/130947 A1 | 8/2016 |
| WO | 2016/130977 A1 | 8/2016 |
| WO | 2016/130988 A1 | 8/2016 |
| WO | 2016/130993 A1 | 8/2016 |
| WO | 2016/130998 A1 | 8/2016 |
| WO | 2016/131001 A1 | 8/2016 |
| WO | 2016/131003 A1 | 8/2016 |
| WO | 2016/131004 A1 | 8/2016 |
| WO | 2017/004455 A1 | 1/2017 |
| WO | 2017/004477 A2 | 1/2017 |
| WO | 2017/023777 A1 | 2/2017 |
| WO | 2017/023820 A1 | 2/2017 |
| WO | 2017/165323 A1 | 9/2017 |
| WO | 2017/165344 A1 | 9/2017 |
| WO | 2017/165345 A1 | 9/2017 |
| WO | 2018/085251 A1 | 5/2018 |
| WO | 2018/085254 A1 | 5/2018 |
| WO | 2018/106824 A1 | 6/2018 |
| WO | 2018/107185 A1 | 6/2018 |
| WO | 2018/136638 A1 | 7/2018 |
| WO | 2018/144998 A1 | 8/2018 |
| WO | 2018/170006 A1 | 9/2018 |
| WO | 2018/200466 A1 | 11/2018 |
| WO | 2018/200471 A1 | 11/2018 |
| WO | 2019/006366 A1 | 1/2019 |
| WO | 2019/006377 A1 | 1/2019 |
| WO | 2019/050649 A1 | 3/2019 |
| WO | 2019/051184 A1 | 3/2019 |
| WO | 2019/070981 A1 | 4/2019 |
| WO | 2019/183284 A1 | 9/2019 |
| WO | 2019/195168 A1 | 10/2019 |
| WO | 2019/221925 A1 | 11/2019 |
| WO | 2019/226570 A1 | 11/2019 |

OTHER PUBLICATIONS

International Preliminary Report on Patentability received for PCT Patent Application No. PCT/US2016/017797, dated Aug. 24, 2017, 7 pages.

Extended European Search Report (includes Supplementary European Search Report and European Search Opinion) received for European Patent Application No. 16749983.9, dated Sep. 21, 2018, 7 pages.

SYSTEMS AND PROCESSES FOR POLYMER PRODUCTION

CROSS-REFERENCE TO RELATED APPLICATIONS

This application is a U.S. national phase patent application of PCT/US2016/017797, filed Feb. 12, 2016, published as WO2016/130947 on Aug. 18, 2016, which claims priority to and the benefit of U.S. Provisional Patent Application No. 62/116,238, filed Feb. 13, 2015, each of which is incorporated herein by reference in its entirety.

FIELD

The present disclosure relates generally to polypropiolactone and methods of producing thereof, and more specifically to polypropiolactone having acrylate end groups and methods for producing thereof, and the use of such polypropiolactone having acrylate end groups in producing acrylic acid.

BACKGROUND

Methods have been described where acrylic acid (AA) is produced via the pyrolysis of polypropiolactone (PPL) (e.g., see U.S. Pat. No. 2,361,036). However, PPL pyrolysis as described in this and related literature does not produce acrylic acid of sufficient purity for direct use in radical polymerization for superabsorbent polymer (SAP) production. Instead, the methods require expensive and energy intensive purification of the acrylic acid before it can be polymerized to produce SAP. There is therefore a need in the art for methods of directly producing glacial acrylic without the need for expensive and energy intensive AA purification.

The pyrolysis of PPL to acrylic acid (AA) presents several challenges for commercialization.

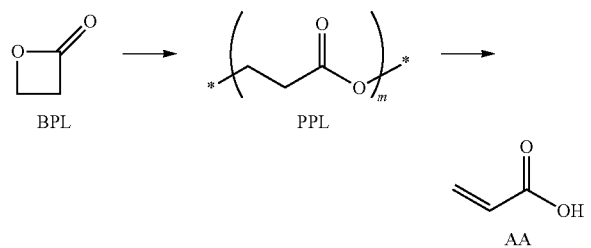

In the above scheme, each * indicates a point of attachment on either side of monomeric units of the PPL polymer. The pyrolysis of PPL to crude or glacial acrylic acid is beset with problems. Although PPL can be prepared from BPL, this conversion may proceed with relatively little control, from batch to batch, in regards to the molecular weight and/or polydispersity of the PPL.

Polymerization inhibitors and anti-foaming agents may be added, to the PPL during pyrolysis, or to acrylic acid once formed, to control reactivity, preserve acrylic acid from degradation, polymerization and/or reduce foaming. However, there is a growing need to produce acrylic acid, particularly glacial acrylic acid, having little or no impurities, and low levels of polymerization inhibitors and/or anti-foaming agents, in order to minimize contamination of downstream polymers, such as SAPs, and end product articles such as diapers.

BRIEF SUMMARY

The systems and processes described herein address various challenges known in the art associated with the pyrolysis of polypropiolactone to crude or glacial acrylic acid at industrial-scale.

Disclosed herein are polypropiolactone compositions comprising polypropiolactone chains of Formula (I) and/or (II), as described below, that provide higher and smoother conversion to acrylic acid upon pyrolysis. Without being bound by theory, it is believed that this improvement may be due, in part, to the lower molecular weights and/or narrow molecular weight distribution of the polypropiolactone compositions comprising polypropiolactone chains of Formula (I) and/or (II), having a high degree of acrylated and/or hydroxylated end groups.

In one aspect, a method is provided for the production of a polypropiolactone composition comprising polypropiolactone chains of Formula (I):

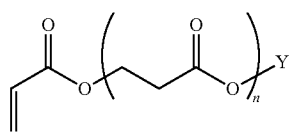

wherein n is an integer from 10 to about 1,000 and Y is either —H or a cation, comprising polymerizing beta propiolactone in the presence of a chain transfer agent of Formula (III):

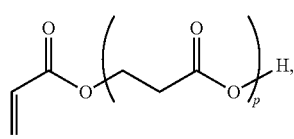

or a salt thereof, or a mixture of any two or more of these, where p is from 0 to 9.

In another aspect, a method is provided for the production of a polypropiolactone composition comprising polypropiolactone chains of Formula (II):

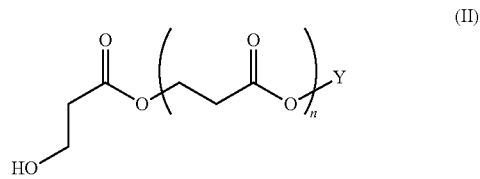

where n is an integer from about 10 to about 1000 and Y is either —H or a cation.

In another aspect, a method is provided for producing acrylic acid, the method comprising heating a polypropiolactone composition containing the polypropiolactone chains of Formula (I) and/or (II). In certain embodiments, at least 90% of polymer chains in the polypropiolactone composition have an acrylate end group of Formula (I) and/or a hydroxyl group of Formula (II). These and other aspects are described in greater detail below.

In some variations, provided is a method for producing a polypropiolactone composition, comprising: combining beta propiolactone and at least one chain transfer agent to produce the polypropiolactone composition, wherein:

the at least one chain transfer agent is at least one compound, or a salt thereof, independently comprising:

(i) an acrylate end group having the structure

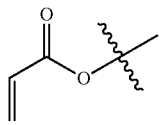

or a hydracrylate end group having the structure

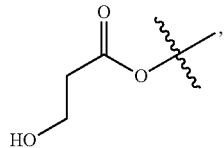 [SMILES: *OC(=O)CCO]

and optionally (ii) a chain comprising one or more units having the structure

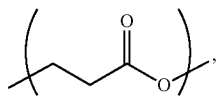

wherein the acrylate end group or the hydracrylate end group caps the alkyl terminus of the chain, and wherein the at least one chain transfer agent independently has a number average molecular weight ($M_n$) of less than about 1000 g/mol; and the polypropiolactone composition comprises polypropiolactone polymers, or salts thereof, independently comprising:

(a) an acrylate end group having the structure

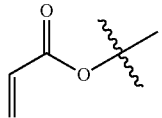

or a hydracrylate end group having the structure

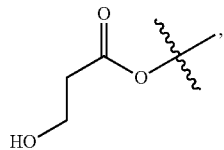 [SMILES: *OC(=O)CCO]

and (b) a polymer chain comprising repeating units having the structure

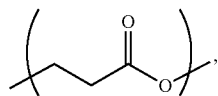

wherein the acrylate end group or the hydracrylate end group caps the alkyl terminus of the polymer chain, and
wherein:
(1) the polypropiolactone polymers, or salts thereof, have an $M_n$ of less than or equal to about 40,000 g/mol; or
(2) the polypropiolactone composition has a polydispersity index (PDI) less than or equal to about 2.0; or
(3) at least 90 wt % of the polypropiolactone composition comprises polypropiolactone polymers, or salts thereof, having either the acrylate end group or the hydracrylate end group, or
any combinations of (1)-(3) above.

In other variations, provided is a method for producing a polypropiolactone composition, comprising: combining beta propiolactone and water to produce the polypropiolactone composition,
wherein the polypropiolactone composition comprises polypropiolactone polymers, or salts thereof, independently comprising:
(a) a hydracrylate end group having the structure

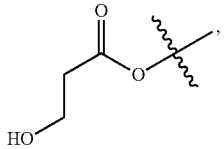 [SMILES: *OC(=O)CCO]

and
(b) a polymer chain comprising repeating units having the structure

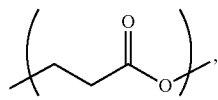

wherein the hydracrylate end group caps the alkyl terminus of the polymer chain, and
wherein:
(1) the polypropiolactone polymers, or salts thereof, have an $M_n$ of less than or equal to about 40,000 g/mol;
(2) the polypropiolactone composition has a PDI less than or equal to about 2.0;
(3) at least 90 wt % of the polypropiolactone composition comprises polypropiolactone polymers, or salts thereof, having the hydracrylate end group, or
any combinations of (1)-(3) above.

In other aspects, provided is a method for producing acrylic acid, comprising heating any of the polypropiolactone compositions described herein to produce the acrylic acid.

In yet other aspects, provided is also a method for producing a superabsorbent polymer, comprising:
pyrolyzing any of the polypropiolactone composition described herein; and
polymerizing the acrylic acid blended with a base in the presence of a radical initiator to produce the superabsorbent polymer.

In some variations, the base is sodium hydroxide.

In certain aspects, provided is a polypropiolactone composition, comprising polypropiolactone polymers, or salts thereof, independently comprising:

(a) an acrylate end group having the structure

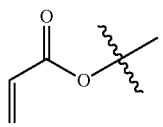

or a hydracrylate end group having the structure

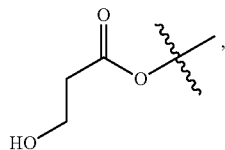 [SMILES: *OC(=O)CCO]

and (b) a polymer chain comprising repeating units having the structure

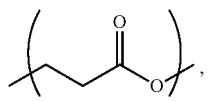

wherein the acrylate end group or the hydracrylate end group caps the alkyl terminus of the polymer chain.

In some variations that can be combined with the foregoing aspect, the polypropiolactone polymers, or salts thereof, have an $M_n$ of less than or equal to about 40,000 g/mol. In other variations that can be combined with the foregoing aspects and variations, the polypropiolactone composition has a PDI less than or equal to about 2.0. In yet other variations that can be combined with the foregoing aspects and variations, at least 90 wt % of the polypropiolactone composition comprises polypropiolactone polymers, or salts thereof, having the acrylate end group or the hydracrylate end group.

Definitions

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987.

The terms "halo" and "halogen" as used herein refer to an atom selected from fluorine (fluoro, —F), chlorine (chloro, —Cl), bromine (bromo, —Br), and iodine (iodo, —I).

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. In some variations, the aliphatic group is unbranched or branched. In other variations, the aliphatic group is cyclic. Unless otherwise specified, in some variations, aliphatic groups contain 1-30 carbon atoms. In certain embodiments, aliphatic groups contain 1-12 carbon atoms. In certain embodiments, aliphatic groups contain 1-8 carbon atoms. In certain embodiments, aliphatic groups contain 1-6 carbon atoms. In certain embodiments, aliphatic groups contain 1-5 carbon atoms, In certain embodiments, aliphatic groups contain 1-4 carbon atoms, in yet other embodiments aliphatic groups contain 1-3 carbon atoms, and in yet other embodiments aliphatic groups contain 1-2 carbon atoms. Suitable aliphatic groups include, for example, linear or branched, alkyl, alkenyl, and alkynyl groups, and hybrids thereof such as (cycloalkyl) alkyl, (cycloalkenyl)alkyl or (cycloalkyl)alkenyl.

The term "heteroaliphatic" as used herein, refers to aliphatic groups wherein one or more carbon atoms are independently replaced by one or more atoms selected from the group consisting of oxygen, sulfur, nitrogen, phosphorus, or boron. In certain embodiments, one or two carbon atoms are independently replaced by one or more of oxygen, sulfur, nitrogen, or phosphorus. Heteroaliphatic groups may be substituted or unsubstituted, branched or unbranched, cyclic or acyclic, and include "heterocycle," "hetercyclyl," "heterocycloaliphatic," or "heterocyclic" groups. In some variations, the heteroaliphatic group is branched or unbranched. In other variations, the heteroaliphatic group is cyclic. In yet other variations, the heteroaliphatic group is acyclic.

The term "unsaturated", as used herein, means that a moiety has one or more double or triple bonds.

The terms "cycloaliphatic", "carbocycle", or "carbocyclic", used alone or as part of a larger moiety, refer to a saturated or partially unsaturated cyclic aliphatic monocyclic, bicyclic, or polycyclic ring systems, as described herein, having from 3 to 12 members, wherein the aliphatic ring system is optionally substituted as defined above and described herein. Cycloaliphatic groups include, for example, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In certain embodiments, the cycloalkyl has 3-6 carbons. The terms "cycloaliphatic", "carbocycle" or "carbocyclic" also include aliphatic rings that are fused to one or more aromatic or nonaromatic rings, such as decahydronaphthyl or tetrahydronaphthyl, where the radical or point of attachment is on the aliphatic ring. In certain embodiments, a carbocyclic groups is bicyclic. In certain embodiments, a carbocyclic group is tricyclic. In certain embodiments, a carbocyclic group is polycyclic.

The term "alkyl," as used herein, refers to a saturated hydrocarbon radical. In some variations, the alkyl group is a saturated, straight- or branched-chain hydrocarbon radicals derived from an aliphatic moiety containing between one and six carbon atoms by removal of a single hydrogen atom. Unless otherwise specified, in some variations, alkyl groups contain 1-12 carbon atoms. In certain embodiments, alkyl groups contain 1-8 carbon atoms. In certain embodiments, alkyl groups contain 1-6 carbon atoms. In certain embodiments, alkyl groups contain 1-5 carbon atoms, In certain embodiments, alkyl groups contain 1-4 carbon atoms, in yet other embodiments alkyl groups contain 1-3 carbon atoms, and in yet other embodiments alkyl groups contain 1-2 carbon atoms. Alkyl radicals may include, for example, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, and dodecyl.

The terms "alkene" and "alkenyl," as used herein, denote a monovalent group having at least one carbon-carbon double bond. In some variations, the alkenyl group is a monovalent group derived from a straight- or branched-chain aliphatic moiety having at least one carbon-carbon double bond by the removal of a single hydrogen atom. Unless otherwise specified, in some variations, alkenyl groups contain 2-12 carbon atoms. In certain embodiments, alkenyl groups contain 2-8 carbon atoms. In certain embodiments, alkenyl groups contain 2-6 carbon atoms. In certain embodiments, alkenyl groups contain 2-5 carbon atoms, In certain embodiments, alkenyl groups contain 2-4 carbon atoms, in yet other embodiments alkenyl groups contain 2-3 carbon atoms, and in yet other embodiments alkenyl groups contain 2 carbon atoms. Alkenyl groups include, for example, ethenyl, propenyl, butenyl, 1-methyl-2-buten-1-yl, and the like.

The term "alkynyl," as used herein, refers to a monovalent group having at least one carbon-carbon triple bond. In some variations, the alkynyl group is a monovalent group derived from a straight- or branched-chain aliphatic moiety having at least one carbon-carbon triple bond by the removal of a single hydrogen atom. Unless otherwise specified, in some variations, alkynyl groups contain 2-12 carbon atoms. In certain embodiments, alkynyl groups contain 2-8 carbon atoms. In certain embodiments, alkynyl groups contain 2-6 carbon atoms. In certain embodiments, alkynyl groups contain 2-5 carbon atoms, In certain embodiments, alkynyl groups contain 2-4 carbon atoms, in yet other embodiments alkynyl groups contain 2-3 carbon atoms, and in yet other embodiments alkynyl groups contain 2 carbon atoms. Representative alkynyl groups include, for example, ethynyl, 2-propynyl (propargyl), and 1-propynyl.

The term "carbocycle" and "carbocyclic ring" as used herein, refers to monocyclic and polycyclic moieties wherein the rings contain only carbon atoms. Unless otherwise specified, carbocycles may be saturated, partially unsaturated or aromatic, and contain 3 to 20 carbon atoms. Representative carbocyles include, for example, cyclopropane, cyclobutane, cyclopentane, cyclohexane, bicyclo[2,2,1]heptane, norbornene, phenyl, cyclohexene, naphthalene, and spiro[4.5]decane.

The term "aryl" used alone or as part of a larger moiety as in "aralkyl", "aralkoxy", or "aryloxyalkyl", refers to monocyclic and polycyclic ring systems having a total of five to 20 ring members, wherein at least one ring in the system is aromatic and wherein each ring in the system contains three to twelve ring members. The term "aryl" may be used interchangeably with the term "aryl ring". In certain embodiments, "aryl" refers to an aromatic ring system which includes, for example, phenyl, naphthyl, and anthracyl, which may bear one or more substituents. Also included within the scope of the term "aryl", as it is used herein, is a group in which an aromatic ring is fused to one or more additional rings, such as benzofuranyl, indanyl, phthalimidyl, naphthimidyl, phenanthridinyl, and tetrahydronaphthyl.

The terms "heteroaryl" and "heteroar-", used alone or as part of a larger moiety, e.g., "heteroaralkyl", or "heteroaralkoxy", refer to groups having 5 to 14 ring atoms, preferably 5, 6, 9 or 10 ring atoms; having 6, 10, or 14 pi (π) electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, for example, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, benzofuranyl and pteridinyl. The terms "heteroaryl" and "heteroar-" as used herein, also include groups in which a heteroaromatic ring is fused to one or more aryl, cycloaliphatic, or heterocyclyl rings, where the radical or point of attachment is on the heteroaromatic ring. Examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and may be saturated or partially unsaturated, and have, in addition to carbon atoms, one or more, preferably one to four, heteroatoms, as defined above. In some variations, the heterocyclic group is a stable 5- to 7-membered monocyclic or 7- to 14-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, for example, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds described herein may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned herein are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

In some chemical structures herein, substituents are shown attached to a bond which crosses a bond in a ring of the depicted molecule. This means that one or more of the substituents may be attached to the ring at any available position (usually in place of a hydrogen atom of the parent structure). In cases where an atom of a ring so substituted has two substitutable positions, two groups may be present on the same ring atom. When more than one substituent is present, each is defined independently of the others, and each may have a different structure. In cases where the substituent shown crossing a bond of the ring is —R, this has the same meaning as if the ring were said to be "optionally substituted" as described in the preceding paragraph.

Suitable monovalent substituents on a substitutable carbon atom of an "optionally substituted" group are independently halogen; —(CH$_2$)$_{0-4}$R°; —(CH$_2$)$_{0-4}$OR°; —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)N(R°)$_2$; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR°; —SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°; —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched)alkylene)O—N(R°)$_2$; or —(C$_{1-4}$ straight or branched)alkylene)C(O)O—N(R°)$_2$, wherein each R° may be substituted as defined below and is independently hydrogen, C$_{1-8}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, and sulfur, or, notwithstanding the definition above, two independent occurrences of R°, taken together with their intervening atom(s), form a 3-12-membered saturated, partially unsaturated, or aryl mono- or polycyclic ring having 0-4 heteroatoms independently selected from nitrogen, oxygen, and sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-4}$C(O)N(R$^\bullet$)$_2$; —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, and sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, and sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, and sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, and sulfur.

Suitable substituents on a substitutable nitrogen of an "optionally substituted" group include —R$^\dagger$, —NR$^\dagger$$_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger$$_2$, —C(S)NR$^\dagger$$_2$, —C(NH)NR$^\dagger$$_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, and sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, and sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, and sulfur.

As used herein, the terms "crude acrylic acid" and "glacial acrylic acid" describe acrylic acid of relatively low and high purity, respectively. Crude acrylic acid (also called technical grade acrylic acid) has a typical minimum overall purity level of 94%, by weight, and can be used to make acrylic esters for paint, adhesive, textile, paper, leather, fiber, and plastic additive applications. Glacial acrylic acid has a typical overall purity level ranging from 98% to 99.99% and can be used to make polyacrylic acid (PAA), or a salt thereof, for superabsorbent polymers (SAPs) in disposable diapers, training pants, adult incontinence undergarments and sanitary napkins. polyacrylic acid is also used in compositions for paper and water treatment, and in detergent co-builder applications. In some variations, acrylic acid has a purity of at least 98%, at least 98.5%, at least 99%, at least 99.1%, at least 99.2%, at least 99.3%, at least 99.4%, at least 99.5%, at least 99.6%, at least 99.7%, at least 99.8%, or at least 99.9%; or between 99% and 99.95%, between 99.5% and 99.95%, between 99.6% and 99.95%, between 99.7% and 99.95%, or between 99.8% and 99.95%.

Suitable salts of PAA include metal salts, such those of any alkali (e.g., $Na^+$, $K^+$) cations, alkaline earth cations. In certain embodiments, the PAA salt is the $Na^+$ salt, i.e., sodium PAA. In certain embodiments, the salt is the $K^+$ salt, i.e., potassium PAA.

Impurities in glacial acrylic acid are reduced to an extent possible to facilitate a high-degree of polymerization to acrylic acid polymers (PAA) and avoid adverse effects from side products in end applications. For example, aldehyde impurities in acrylic acid hinder polymerization and may discolor the polymerized acrylic acid. Maleic anhydride impurities form undesirable copolymers which may be detrimental to polymer properties. Carboxylic acids, e.g., saturated carboxylic acids that do not participate in the polymerization, can affect the final odor of PAA or SAP-containing products and/or detract from their use. For example, foul odors may emanate from SAP that contains acetic acid or propionic acid and skin irritation may result from SAP that contains formic acid.

The reduction or removal of impurities from propylene-based acrylic acid is costly, whether to produce propylene-based crude acrylic acid or propylene-based glacial acrylic acid. Such costly multistage distillations and/or extraction and/or crystallizations steps are generally employed (e.g., as described in U.S. Pat. Nos. 5,705,688 and 6,541,665). Notable impurities from propylene-based acrylic acid that are reduced and/or eliminated from the disclosed compositions include, for example, aldehyde impurities and products or byproducts of propylene oxidation.

As used herein, the term "product or byproduct of propylene oxidation" or "compound that derives from the oxidation of propylene" are used interchangeably to refer to products and byproducts of propylene oxidation including, for example, $C_1$ compounds such as formaldehyde, and formic acid; $C_2$ compounds such as acetaldehyde, acetic acid; $C_3$ compounds such as propylene, allyl alcohol, acrolein (i.e., propenal), propanol, isopropyl alcohol, acetone, propionic acid; $C_4$ compounds such as maleic anhydride; and $C_5$ compounds such as furfural, etc.

As used herein, the term "aldehyde impurity" includes any of the aldehydes in the preceding paragraph.

As used herein, the term "substantially free" means, in some variations, less than 5 wt %, 1 wt %, 0.1 wt %, 0.01 wt %, or a range including any two of these values, or less than 10,000 ppm, 1,000 ppm, 500 ppm, 100 ppm, 50 ppm, 10 ppm, or a range including any two of these values. In one variation, a composition that is substantially free of Compound A has less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.05%, less than 0.01%, or less than 0.001%, by weight, or a range including any two of the aforementioned values, of Compound A.

Stabilizers are commonly used to preserve acrylic acid. As used herein, the term "stabilizer" includes any radical polymerization inhibitor or an anti-foaming agent. Acrylic acid is susceptible to unwanted Michael addition to itself and to unwanted free-radical polymerization with itself, which may be counteracted by addition of polymerization inhibitors to the acrylic acid. Suitable polymerization inhibitors include, for example, hydroquinone monomethyl ether, MEHQ, alkylphenols, such as o-, m- or p-cresol (methylphenol), 2-tert-butyl-4-methylphenol, 6-tert-butyl-2,4-dimethylphenol, 2,6-di-tert-butyl-4-methylphenol, 2-tert-butylphenol, 4-tert-butylphenol, 2,4-di-tert-butylphenol and 2-methyl-4-tert-butylphenol and hydroxyphenols such as hydroquinone, catechol, resorcinol, 2-methylhydroquinone and 2,5-di-tert-butylhydroquinone. Examples of anti-foaming agents include silicones (e.g., polydimethylsiloxanes), alcohols, stearates, and glycols.

As used herein, the terms "polydispersity" and "polydispersity index" (PDI) refer interchangeably to a measure of the distribution of molecular mass in a given polymer sample. PDI is calculated as the weight average molecular weight ($M_w$) divided by the number average molecular weight ($M_n$). $M_n$ is the total weight of all the polymer molecules in a sample, divided by the total number of polymer molecules in a sample. $M_w$ accounts for the fact that bigger polymers contain more of the total mass of polymer in a sample than the smaller polymers do. For example, $M_n$ for a hypothetical mixture of four polymer chains having the following molecular weights, in g/mol, 700,000, 10,000, 12,000 and 1,500 (divided by 4) is 180,875. In contrast, $M_w$ is calculated by multiplying the molecular weight of each polymer chain by the percentage of total weight that each polymer chain contributes to the sample (700,000×0.968)+(10,000×0.014)+(12,000×0.017)+(1,500×0.0021)=677,604.

PDI indicates the distribution of individual molecular masses in a polymer sample. The PDI has a value equal to or greater than 1, and as the polymer chains approach uniform chain length, the PDI approaches unity (1). PDI may be calculated using routine methods, such as gel permeation chromatography (also known as size exclusion chromatography), light scattering measurements such as dynamic light scattering, and/or by direct measurement via mass spectrometry using MALDI or ESI-MS.

As used herein, the term "superabsorbent polymer" (SAP) refers to a water-swellable, water-insoluble polymer capable, under the most favorable conditions, of absorbing at least about 10 times its weight in an aqueous solution containing 0.9 weight percent sodium chloride. A SAP's ability to absorb water may depend on the ionic concentration of the aqueous solution. In deionized and distilled water, a SAP may absorb 500 times its weight (from 30 to 60 times its own volume) and can become up to 99.9% liquid, but when put into a 0.9% saline solution, the absorbency may drop to 50 times its weight.

The term "acrylate" or "acrylates" as used herein refer to any acyl group having a vinyl group adjacent to the acyl carbonyl. The terms encompass mono-, di- and tri-substituted vinyl groups. Acrylates may include, for example, acrylate, methacrylate, ethacrylate, cinnamate (3-phenylacrylate), crotonate, tiglate, and senecioate.

The term "polymer", as used herein, refers to a molecule comprising multiple repeating units. In some variations, the polymer is a molecule of high relative molecular mass, the structure of which comprises the multiple repetition of units derived, actually or conceptually, from molecules of low relative molecular mass. In certain embodiments, a polymer is comprised of only one monomer species (e.g., polyethylene oxide). In certain embodiments, the polymer is a copolymer, terpolymer, heteropolymer, block copolymer, or tapered heteropolymer of one or more epoxides. In one variation, the polymer may be a copolymer, terpolymer, heteropolymer, block copolymer, or tapered heteropolymer of two or more monomers.

In some variations, the term "epoxide", as used herein, refers to a substituted or unsubstituted oxirane. Substituted oxiranes include monosubstituted oxiranes, disubstituted oxiranes, trisubstituted oxiranes, and tetrasubstituted oxiranes. Such epoxides may be further optionally substituted as defined herein. In certain embodiments, epoxides comprise a single oxirane moiety. In certain embodiments, epoxides comprise two or more oxirane moieties.

As used herein, the term "about" preceding one or more numerical values means the numerical value ±5%. It should be understood that reference to "about" a value or parameter herein includes (and describes) embodiments that are directed to that value or parameter per se. For example, description referring to "about x" includes description of "x" per se.

DETAILED DESCRIPTION

Pyrolysis of relatively high molecular weight PPL and/or polydisperse PPL is observed to yield acrylic acid contaminated with a relatively high degree of unwanted side products and/or decomposition products. Without being bound by theory, it is believed that the heat required to efficiently pyrolyze relatively high molecular weight PPL species exceeds that needed to pyrolyze low molecular weight PPL species, leading to unwanted degradation products.

Thus, in some aspects, described herein are PPL compositions comprising polypropiolactone polymers, or salts thereof. In some embodiments, the polypropiolactone polymers, or salts thereof, independently comprise:

(a) an acrylate end group having the structure

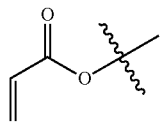

or a hydracrylate end group having the structure

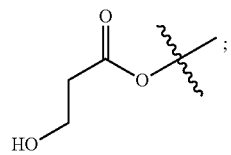

and (b) a polymer chain comprising repeating units having the structure

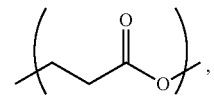

wherein the acrylate end group or the hydracrylate end group caps the alkyl terminus of the polymer chain.

It should generally be understood that the "alkyl terminus" of the polymer chain refers to the following:

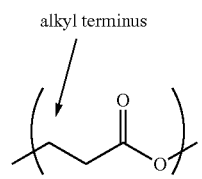

It should further be understood that PPL compositions described herein may include a mixture of polypropiolactone polymers, or salts thereof. For example, polypropiolactone polymers, or salts thereof, synthesized with hydroxylate end groups may undergo partial dehydration to yield a mixture of polypropiolactone polymers, or salts thereof, with acrylate and hydracrylate end groups.

In certain embodiments, described herein are PPL compositions comprising chains of Formula (I) and/or (II), as described herein, that provide higher and smoother conversion to acrylic acid. Without being bound by theory, it is believed this may be due, in part, to the lower molecular weights and/or narrow molecular weight distribution of the polymer compositions provided herein.

In some aspects, provided are polypropiolactone compositions containing polypropiolactone chains of Formula (I), having an acrylate end group, that can more effectively and efficiently convert (e.g., via pyrolysis) to acrylic acid than conventional PPL, which lacks or substantially lacks acrylate end groups.

Depicted below is a general reaction scheme that shows an exemplary two-step process to produce acrylic acid using the polypropiolactone compositions described herein. In the first step depicted in the general reaction scheme, beta propiolactone is combined with an acrylate-containing molecule (e.g., an acrylate-containing chain transfer agent) to produce a polypropiolactone of Formula (I), which can then be heated to produce acrylic acid.

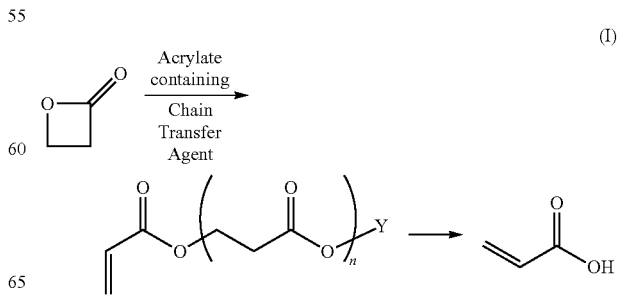

(I)

In some variations, the acrylate-containing molecule is acrylic acid.

In other aspects, further provided are polypropiolactone compositions containing polypropiolactone chains of Formula (II), having hydroxyl end groups, that more effectively and efficiently convert (e.g., via pyrolysis) to acrylic acid than conventional PPL, which lacks or substantially lacks hydroxyl end groups.

Depicted below is a general reaction scheme that shows another exemplary two-step process to produce acrylic acid using the polypropiolactone compositions described herein. In the first step depicted in the general reaction scheme, beta propiolactone is combined with water or a hydracrylic acid derivative to produce a polypropiolactone of Formula (II), which can then be converted to acrylic acid.

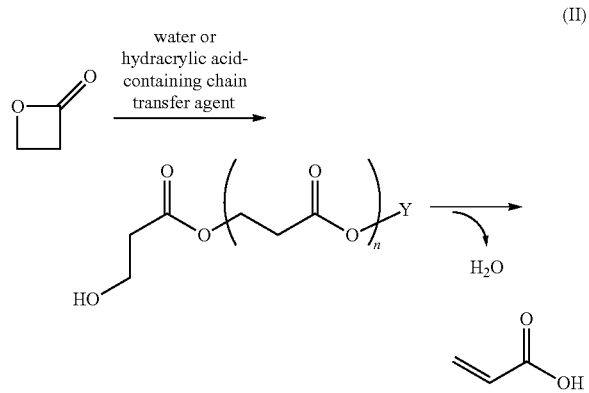

As used herein, the term "PPL that substantially lacks acrylate or hydroxyl end groups" refers to PPL compositions where fewer than 40%, 20%, 10%, 5%, 2% or 1% of the chains in the composition contain such acrylate or hydroxyl end groups.

For the polypropiolactone chains of Formula (I) or (II), n is an integer from 10 to about 1,000 and Y is —H or a cation. Suitable cations include any alkali (e.g., Na⁺, K⁺), alkaline earth cation or an organic cation (e.g., nitrogen-, sulfur-, phosphorous- or arsenic-containing) cations, such as those described herein. In certain embodiments, the cation is Na⁺.

In certain embodiments, the polypropiolactone chains of Formula (I) or (II) have a relatively low molecular weight (e.g., less than or equal to about 40,000 g/mol) and/or polydispersity (e.g., a PDI of less than or equal to about 2.0). Also provided are methods for making PPL compositions containing polymer chains of Formula (I) or (II) and for carrying out pyrolysis of the same to produce acrylic acid.

Compositions

In some aspects, provided are polypropiolactone (PPL) compositions, comprising polypropiolactone polymers, or salts thereof. In one aspect, the polypropiolactone polymers, or salts thereof, described herein include PPL polymer chains having acrylate end groups.

In some variations, the polypropiolactone polymers, or salts thereof, independently comprise:

(a) an acrylate end group having the structure

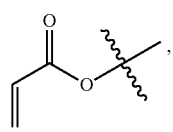 [SMILES: *OC(=O)C=C]

and (b) a polymer chain comprising repeating units having the structure

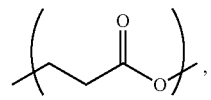

wherein the acrylate end group caps the alkyl terminus of the polymer chain.

In some variations of the foregoing, the PPL composition comprises salts of the polypropiolactone polymers. In certain variations, the salt of the polypropiolactone polymers comprises a Group I or Group II cation. In one variation, the salt of the polypropiolactone polymers comprises a sodium or potassium cation.

In some variations of the foregoing, (i) the polypropiolactone polymers, or salts thereof, have an $M_n$ of less than or equal to about 40,000 g/mol; (ii) the polypropiolactone composition has a PDI less than or equal to about 2.0; or (iii) at least 90 wt % of the polypropiolactone composition comprises polypropiolactone polymers, or salts thereof, having the acrylate end, or any combination of (i)-(iii).

In certain embodiments, provided are PPL compositions comprising polypropiolactone chains of Formula (I):

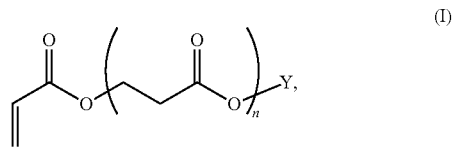

wherein:

n is an integer from about 10 to about 1000; and
Y is —H or a cation.

In some variations, provided are polypropiolactone (PPL) compositions, comprising polypropiolactone chains of Formula (I):

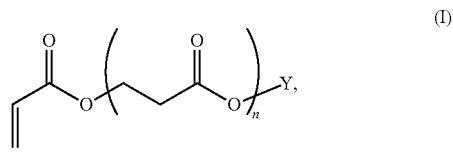

wherein:

n is an integer; and
Y is —H or a cation, and wherein the number average molecular weight of the PPL compositions is in the range from about 800 g/mol to about 72,000 g/mol.

In certain embodiments, n is an integer from about 10 (e.g. polypropiolactone chains having a molecular weight of about 800 g/mol) to about 500 (e.g. polypropiolactone chains having a molecular weight of about 36,000 g/mol).

In certain embodiments, Y is Na⁺. In certain embodiments, Y is hydrogen. In certain embodiments, Y is an organic cation containing phosphorous, nitrogen or sulfur, or any combinations thereof.

In certain embodiments, the polypropiolactone (PPL) compositions include polypropiolactone chains of Formula (Ia)

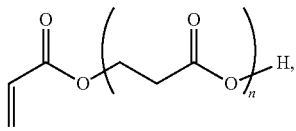

(Ia)

wherein n is an integer from about 10 to about 1000. In certain embodiments, the polypropiolactone (PPL) compositions include polypropiolactone chains of Formula (Ia) where n is an integer from about 10 to about 500.

In another aspect, the polypropiolactone polymers, or salts thereof, described herein include PPL polymer chains having hydracrylate end groups. In some variations, the polypropiolactone polymers, or salts thereof, independently comprise:

(a) a hydracrylate end group having the structure

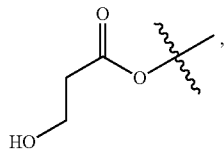

and (b) a polymer chain comprising repeating units having the structure

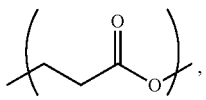

wherein the hydracrylate end group caps the alkyl terminus of the polymer chain.

In some variations of the foregoing, the PPL composition comprises salts of the polypropiolactone polymers. In certain variations, the salt of the polypropiolactone polymers comprises a Group I or Group II cation. In one variation, the salt of the polypropiolactone polymers comprises a sodium or potassium cation. In one variation, the salt of the polypropiolactone polymers comprises an organic cation. In certain variations the salt of the polypropiolactone polymers comprises an ammonium salt or a phosphonium salt.

In some variations of the foregoing, (i) the polypropiolactone polymer compositions have an $M_n$ less than or equal to about 40,000 g/mol; (ii) the polypropiolactone composition has a PDI less than or equal to about 2.0; or (iii) at least 90 wt % of the polypropiolactone composition comprises polypropiolactone polymers, or salts thereof, having the hydracrylate end group, or any combination of (i)-(iii).

In certain embodiments, the PPL compositions described herein comprise polypropiolactone chains of Formula (II)

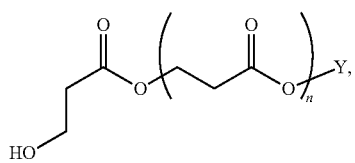

(II)

wherein:
n is an integer from about 10 to about 1000; and
Y is —H or a cation.

In some variations, the PPL compositions described herein comprise polypropiolactone chains of Formula (II)

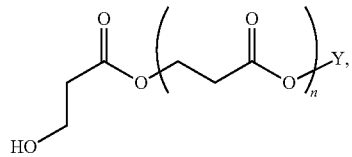

(II)

wherein:
n is an integer; and
Y is —H or a cation,
wherein the polypropiolactone compositions have an $M_n$ from about 800 g/mol to about 72,000 g/mol.

In certain embodiments, n is an integer from about 10 (e.g. polypropiolactone chains having a molecular weight of about 800 g/mol) to about 500 (e.g. polypropiolactone chains having a molecular weight of about 36,000 g/mol).

In certain embodiments, Y is $Na^+$. In certain embodiments, Y is hydrogen. In one variation, Y is an organic cation. In certain embodiments Y is an ammonium salt. In certain embodiments Y is a phosphonium salt.

In certain embodiments, the provided PPL compositions comprise a mixture PPL chains having different Y groups. In certain embodiments, the compositions comprise a mixture of polypropiolactone chains where Y is —H along with polypropiolactone chains where —Y is a cation. In certain embodiments of such compositions, in a majority of the chains —Y is —H. In certain embodiments, at least 50% of the chains have an —H end group. In certain embodiments, at least 60%, at least 75%, at least 80%, at least 85%, at least 90%, or at least 95% of the polymer chains have an —H end group, with the remainder of the PPL chains having a cationic —Y group. In other embodiments of such compositions, in a majority of the PPL chains —Y is a cation. In certain embodiments, at least 50% of the chains have a cationic end group. In certain embodiments, at least 60%, at least 75%, at least 80%, at least 85%, at least 90%, or at least 95% of the chains comprise a cationic Y group, with the remainder of the PPL chains having —H as the —Y group. In certain embodiments of such compositions, the cationic chain ends comprise a sodium cation. In certain embodiments of such compositions, the cationic chain ends comprise an ammonium cation.

In certain embodiments, provided are PPL compositions comprising polypropiolactone polymers, or salts thereof, having acrylate or hydracrylate end groups, including a polypropiolactone chain of Formula (I) and/or (II). In certain embodiments, such polypropiolactone polymers, or salts thereof, including the polypropiolactone chain of Formula (I) and/or (II), are at least 20%, 30%, 40%, 50%, 60%, 70%, 80%, 90%, 95% or 99% pure, or a range including any two of these values. In certain embodiments, such polypropiolactone polymers, or salts thereof, including the polypropiolactone chain of Formula (I) and/or (II), are at least 20%, 30%, 40%, 50%, 60%, 70%, 80%, 90%, 95% or 99% pure on a wt/wt % basis, or a range including any two of these values, relative to PPL polymer without an acrylate or hydroxyl end group.

In certain embodiments, such polypropiolactone polymers, or salts thereof, including the polypropiolactone chain of Formula (I) and/or (II), are at least 80%, 85%, or at least 90%, pure on a wt/wt % basis, or a range including any two of these values, relative to PPL polymer without an acrylate or hydroxyl (or hydracrylate) end group. In certain embodiments, such polypropiolactone polymers, or salts thereof, including the polypropiolactone chain of Formula (I) and/or (II), are at least 95%, 96%, 97%, 97.5%, 98% 98.5% or 99% pure on a wt/wt % basis, or a range including any two of these values, relative to PPL polymer without an acrylate or hydroxyl (or hydracrylate) end group. In certain embodiments, such polypropiolactone polymers, or salts thereof, including the polypropiolactone chain of Formula (I) and/or (II), are at least 99%, 99.1%, 99.2%, 99.4%, 99.5%, 99.6%, 99.7%, 99.8%, or 99.9%, pure on a wt/wt % basis, or a range including any two of these values, relative to PPL polymer without an acrylate or hydroxyl (or hydracrylate) end group.

In certain embodiments, provided is a polypropiolactone composition comprising at least 20 wt % of the polypropiolactone polymers, or salts thereof, described herein, including polypropiolactone chain of Formula (I) and/or (II). In certain embodiments, the polypropiolactone composition comprises at least 30 wt %, 40 wt %, 50 wt %, 60 wt %, 70 wt %, 80 wt % or 90 wt % of the polypropiolactone polymers, or salts thereof, described herein, including polypropiolactone chain of Formula (I) and/or (II), or a range including any two of these values, relative to the wt % of the composition. In some variations, the polypropiolactone composition comprises at 95 wt %, at least 96 wt %, at least 97 wt %, at least 98 wt %, at least 99 wt %, at least 99.1%, at least 99.2 wt %, at least 99.3 wt %, at least 99.4 wt %, at least 99.5 wt %, at least 99.6 wt %, at least 99.7 wt %, at least 99.8 wt %, or at least 99.9 wt %, or a range including any two of these values, relative to the wt % of the composition, of the polypropiolactone polymers, or salts thereof, described herein, including polypropiolactone chain of Formula (I) and/or (II).

In addition, according to certain embodiments herein, the polypropiolactone compositions have a high proportion (wt/wt %) of polypropiolactone polymers, or salts thereof, having acrylate or hydroxyl (or hydracrylate) end groups, including polypropiolactone chain of Formula (I) and/or (II), relative to PPL without acrylate or hydroxyl (or hydracrylate) end groups. In certain embodiments, the polypropiolactone compositions have about 30 wt %, 40 wt %, 50 wt %, 60 wt %, 70 wt %, 80 wt %, 90 wt %, 95 wt %, 99 wt % or 100 wt %, or a range including any two of these values, of polypropiolactone polymers, or salts thereof, having acrylate or hydroxyl (or hydracrylate) end groups, including polypropiolactone chain of Formula (I) and/or (II), relative to about 70 wt %, 60 wt %, 50 wt %, 40 wt %, 30 wt %, 20 wt %, 10 wt %, 5 wt %, 1 wt % or 0 wt %, or a range including any two of these values, of PPL without acrylate or hydroxyl (or hydracrylate) end groups. In some variations, at least 95 wt %, at least 96 wt %, at least 97 wt %, at least 98 wt %, at least 99 wt %, at least 99.1%, at least 99.2 wt %, at least 99.3 wt %, at least 99.4 wt %, at least 99.5 wt %, at least 99.6 wt %, at least 99.7 wt %, at least 99.8 wt %, or at least 99.9 wt %, or a range including any two of these values, of the polypropiolactone composition comprises polypropiolactone polymers, or salts thereof, having acrylate or hydroxyl (or hydracrylate) end groups.

In certain embodiments, the polypropiolactone polymers, or salts thereof, having acrylate or hydracrylate end groups, including polypropiolactone chains of Formula (I) and/or (II), have a relatively low molecular weight, for example, less than or equal to about 40,000 g/mol. In certain embodiments, molecular weight is $M_w$. In certain embodiments, molecular weight is $M_n$. In certain embodiments, the polypropiolactone polymers, or salts thereof, having acrylate or hydracrylate end groups, including polypropiolactone chains of Formula (I) and/or (II), have a molecular weight ($M_w$ or $M_n$) of less than or equal to about 35,000 g/mol, 30,000 g/mol, 25,000 g/mol, 20,000 g/mol, 15,000 g/mol, 10,000 g/mol, 5,000 g/mol, 4,000 g/mol, 3,000 g/mol, 2,000 g/mol or 1,000 g/mol, or a range including any two of these values. In certain variations, the polypropiolactone polymers, or salts thereof, having acrylate or hydracrylate end groups, including polypropiolactone chains of Formula (I) and/or (II), have an $M_n$ of between 1,000 g/mol and 35,000 g/mol, between 1,000 g/mol and 30,000 g/mol, between 1,000 g/mol and 25,000 g/mol, between 1,000 g/mol and 20,000 g/mol, between 1,000 g/mol and 15,000 g/mol, or between 1,000 g/mol and 10,000 g/mol.

In certain embodiments, in the polypropiolactone chains of Formula (I) and/or (II), n is an integer from 10 to about 1,000. In certain embodiments, n is an integer from 10 to about 20, from 20 to about 30, from 30 to about 40, from 40 to about 50, from 50 to about 60, from 60 to about 70, from 70 to about 80, from 80 to about 90, from 90 to about 100, from 100 to about 150, from 150 to about 200, from 200 to about 250, from 250 to about 300, from 300 to about 350, from 350 to about 400, from 400 to about 450, from 450 to about 500, from 500 to about 1,000, or a range including any two of these values.

In certain embodiments, the PPL compositions containing polypropiolactone polymers, or salts thereof, having acrylate or hydracrylate end groups, including chains of Formula (I) and/or (II), have a relatively low polydispersity index (PDI), for example, less than or equal to about 2.0. PDI is calculated as the weight average molecular weight ($M_w$) divided by the number average molecular weight ($M_n$). In certain embodiments, the PPL compositions have a PDI of less than or equal to about 1.9, 1.8, 1.7, 1.6, 1.5, 1.4, 1.3, 1.2 or 1.1, or have a PDI within a range including any two of these values. In certain embodiments, the PPL compositions have a PDI of about 1.5 to 1.0. In certain embodiments, the PPL compositions have a PDI of about 1.2 to 1.0. In certain embodiments, the PPL compositions have a PDI of about 1.1 to 1.0. In certain embodiments, the PPL compositions have a PDI of about 1.0. In certain embodiments, the PPL compositions have a PDI of about 1.5.

It should generally be understood that the variations of molecular weight (including $M_n$), the PDI and the amount of polypropiolactone polymers, or salts thereof, having acrylate or hydracrylate end groups described herein may be combined with each other as if each and every combination were individually listed. Further, the variations of molecular weight (including $M_n$), the PDI and the amount of polypropiolactone polymers, or salts thereof, having acrylate or hydracrylate end groups described herein may be combined with any of the variations regarding the polypropiolactone chains (including polypropiolactone chains having formula I and/or II), as if each and every combination were individually listed.

For example, in certain embodiments, provided is a polymer composition comprising polypropiolactone chains having formula I and/or II:

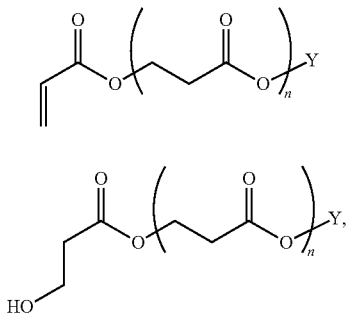

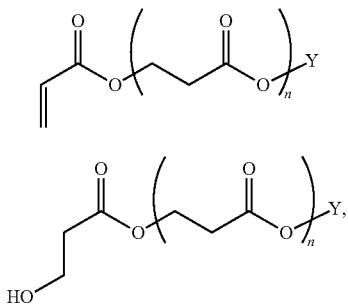

wherein each of n and —Y is as defined above and in the classes and subclasses herein, and wherein the polymer composition has:

(i) an $M_n$ between 1,000 and 10,000 g/mol; or (ii) a PDI of less than 2; or (iii) greater than 95 wt % of polypropiolactone chains having formula I and/or II; or any combinations of (i)-(iii) above.

In some variations, provided is a polymer composition comprising polypropiolactone chains having formula I and/or II:

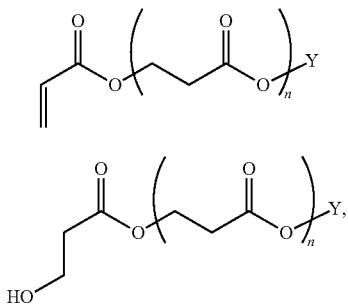

wherein each of n and —Y is as defined above and in the classes and subclasses herein, and wherein the polymer composition has:

(i) an $M_n$ between 1,000 and 3,000 g/mol; or (ii) a PDI of less than 1.7; or (iii) greater than 98 wt % of polypropiolactone chains having formula I and/or II; or any combinations of (i)-(iii) above.

In other variations, provided is a polymer composition comprising polypropiolactone chains having formula I and/or II:

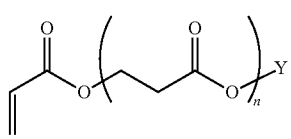

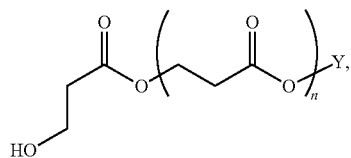

wherein each of n and —Y is as defined above and in the classes and subclasses herein, and wherein the polymer composition has:

(i) an $M_n$ between 1,000 and 5,000 g/mol; or (ii) a PDI of between 1 and 2; or (iii) greater than 99 wt % of polypropiolactone chains having formula I and/or II; or any combinations of (i)-(iii) above.

In other embodiments, the polypropiolactone chains in the polymer composition are predominantly polypropiolactone chains of formula I.

In other embodiments, the $M_n$ of the polypropiolactone chains in the polymer composition is between about 1,000 and 4,000 g/mol.

In other embodiments, the PDI of the polymer composition is less than about 1.7.

In another aspect, provided is a reaction stream comprising any of the polypropiolactone polymers, or salts thereof, described herein. For example, in some variations, provided is a reaction stream comprising polypropiolactone chains of Formula (I):

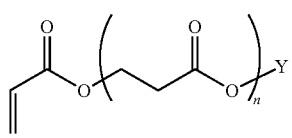

wherein n is an integer from 10 to about 1,000, and Y is either —H or a cation, and wherein the reaction stream produces acrylic acid at a rate of at least about 500 kg/hr. The reaction stream corresponds to a solution of the compound that enters or exits a reactor.

Methods for Preparing PPL Compositions Containing Chains of Formula (I) and/or Formula (II)

In some aspects, provided is a method for producing a polypropiolactone composition, comprising: combining beta propiolactone and at least one acrylate-containing chain transfer agent to produce the polypropiolactone composition. For example, the acrylate-containing chain transfer agent may be a compound, or a salt thereof, comprising an acrylate end group having the structure

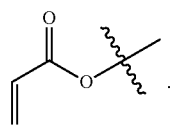 [SMILES: *OC(=O)C=C]

In some variations, the acrylate-containing chain transfer agent may be a compound having an acrylate end group, and a chain comprising one or more units having the structure

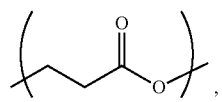

wherein the acrylate end group caps the alkyl terminus of the chain.

In some variations of the foregoing, the chain transfer agent has a number average molecular weight ($M_n$) of less than about 1000 g/mol, less than about 900 g/mol, less than about 800 g/mol, less than about 700 g/mol, less than about 600 g/mol, less than about 500 g/mol, less than about 400 g/mol, less than about 300 g/mol, less than about 200 g/mol, less than about 100 g/mol, less than about 75 g/mol, or less than about 50 g/mol; or between 50 g/mol and 1000 g/mol, between 50 g/mol and 900 g/mol, between 50 g/mol and 800 g/mol, between 50 g/mol and 700 g/mol, between 50 g/mol and 600 g/mol, between 50 g/mol and 500 g/mol, between 50 g/mol and 400 g/mol, between 50 g/mol and 300 g/mol, between 50 g/mol and 200 g/mol, between 50 g/mol and 100 g/mol, or between 50 g/mol and 75 g/mol.

In one aspect, a method is provided for the production of a composition comprising polypropiolactone chains of Formula (I):

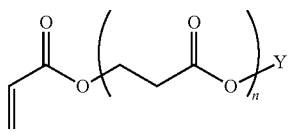

(I)

where n is an integer from 10 to about 1,000 and Y is either —H or a cation, comprising polymerizing beta propiolactone in the presence of a chain transfer agent of Formula (III):

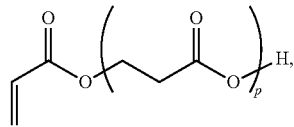

(III)

or a salt thereof, or a mixture of any two or more of these, where p is from 0 to 9.

In some variations, provided is a method for producing a polypropiolactone composition comprising polypropiolactone chains of Formula (I) as described herein, the method comprising combining beta propiolactone and at least one compound of Formula (III), or a salt thereof, as described herein to produce the polypropiolactone composition.

Chain Transfer Agent

The methods described herein produce PPL compositions comprising high proportions (e.g., at least about 30 wt %, 40 wt %, 50 wt %, 60 wt %, 70 wt %, 80 wt %, or 90 wt %) of the polypropiolactone polymers, or salts thereof, having acrylate or hydracrylate end groups, including polypropiolactone chains of Formula (I), relative to polypropiolactone chains without acrylate or hydracrylate end groups. In certain embodiments, at least 90% of polymer chains in the composition have an acrylate or hydracrylate end group. In certain embodiments, at least 90% of polymer chains in the composition conform to Formula (I). In certain embodiments, the composition has a polydispersity index (PDI) of less than 2.

In certain embodiments, the methods comprise polymerizing BPL in the presence of a chain transfer agent (CTA), wherein the chain transfer agent is a compound of Formula (III):

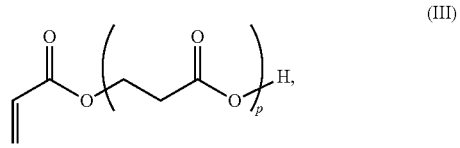

(III)

or a salt thereof, or a mixture of any two or more of these, where p is from 0 to 9. In certain embodiments p is from 0 to 5. In certain embodiments, p is 0, i.e., acrylic acid. In certain embodiments, p is 1. In certain embodiments, p is 2. In certain embodiments, p is 3. In certain embodiments, p is 4. In certain embodiments, p is 5. In certain embodiments, p is 6. In certain embodiments, p is 7. In certain embodiments, p is 8. In certain embodiments, p is 9. In certain embodiments, where the chain transfer agent of Formula (III) is an oligomer, the chain transfer agent has a number average molecular weight of about 200 g/mol, about 300 g/mol, about 400 g/mol, about 500 g/mol, about 600 g/mol or about 700 g/mol or is within a range bounded by any two of these values.

In some variations, the chain transfer agent is at least one compound, or a salt thereof, independently comprising:

(i) an acrylate end group having the structure

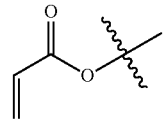 [SMILES: *OC(=O)C=C]

or a hydracrylate end group having the structure

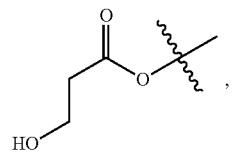

and optionally (ii) a chain comprising one or more units having the structure

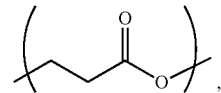

wherein the acrylate end group or the hydracrylate end group caps the alkyl terminus of the chain.

Suitable salts of the chain transfer agents described herein include those of any alkali (e.g., $Na^+$, $K^+$) cations, alkaline earth cations or nitrogen- or phosphorous-containing (e.g., ammonium, alkyl-, dialky-l, trialkyl-, tetraalkyl-ammonium, or phosphonium) cations, such as those described herein. In certain embodiments, the salt is the Na+ salt, such a sodium acrylate. In certain embodiments, the salt is the K+ salt, such a potassium acrylate.

In certain embodiments, use of the chain transfer agent of Formula (III), and incorporation of an acrylate group onto many, most or substantially all chain ends, provides controlled production of the Polypropiolactone chains of Formula (I), having relatively short chain lengths and in compositions having lower PDI, which in turn allows for a more controlled pyrolysis of the PPL composition relative to PPL that substantially lacks acrylate end groups.

In certain embodiments, the chain transfer agent is acrylic acid or a salt thereof. In certain embodiments of the method, the chain transfer agent is acrylic acid dimer,

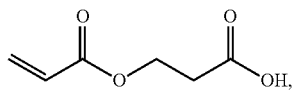

or a salt thereof. In certain embodiments of the method, the chain transfer agent is acrylic acid trimer,

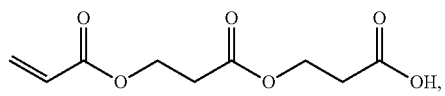

or a salt thereof.

In certain embodiments, the chain transfer agent is combined with BPL in a molar ratio of about 1:5000 chain transfer agent:BPL to about 1:10 chain transfer agent:BPL. In certain embodiments the molar ratio of chain transfer agent:BPL is about 1:5,000, 1:2500, 1:1000, 1:500, 1:200, 1:100, 1:20, 1:10, or a range including any two of these ratios.

In certain embodiments, the beta propiolactone is contacted with the chain transfer agent at a temperature greater than 50° C. In certain embodiments, the temperature is in the range from 50° C. to about 250° C. In certain embodiments, the temperature is in the range from 100° C. to about 200° C. In certain embodiments, the temperature is in the range from 100° C. to about 180° C. In certain embodiments, the temperature is in the range from 120° C. to about 160° C. In certain embodiments, the temperature is in the range from 140° C. to about 180° C.

Hydroxylated Polypropiolactone Chains

In certain aspects, provided is a method for producing a polypropiolactone composition, comprising: combining beta propiolactone and water to produce the polypropiolactone composition. In some variations, the polypropiolactone composition comprises polypropiolactone polymers, or salts thereof, independently comprising:

(a) a hydracrylate end group having the structure

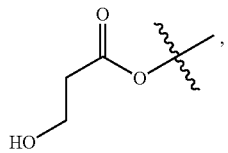

and (b) a polymer chain comprising repeating units having the structure

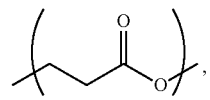

wherein the hydracrylate end group caps the alkyl terminus of the polymer chain.

In another aspect, provided are methods for preparing PPL compositions comprising high proportions (e.g., at least about 30 wt %, 40 wt %, 50 wt %, 60 wt %, 70 wt %, 80 wt %, 90 wt %) of polypropiolactone polymers, or salts thereof, having hydracrylate end groups, including polypropiolactone chains of Formula (II) relative to polypropiolactone chains without hydroxyl end groups. In certain embodiments, the method comprises polymerizing BPL in the presence of water.

(II)

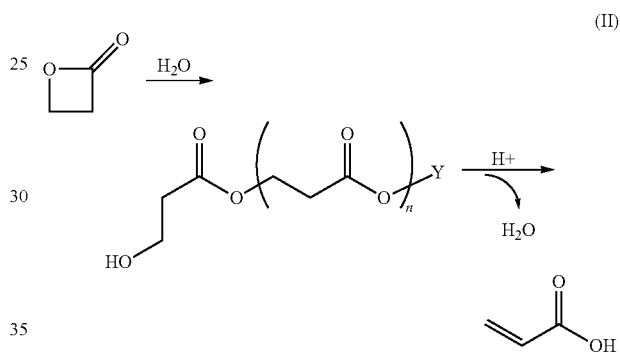

In certain embodiments, the water is combined with BPL in a molar ratio of about 1:5000 water:BPL to about 1:10 water:BPL. In certain embodiments the molar ratio of water:BPL is about 1:5,000, 1:2500, 1:1000, 1:500, 1:200, 1:100, 1:20, 1:10, or a range including any two of these ratios.

In certain embodiments, the use of water and incorporation of a hydroxyl group onto many, most or substantially all chain ends, provides controlled production of the Polypropiolactone chains of Formula (II), having relatively short chain lengths and in compositions having lower PDI, which in turn allows for a more controlled pyrolysis of the PPL compositions relative to PPL that substantially lacks such hydroxyl end groups.

In certain embodiments, the methods comprise polymerizing BPL in the presence of a chain transfer agent (CTA), wherein the chain transfer agent is a compound of Formula (IIIa):

(IIIa)

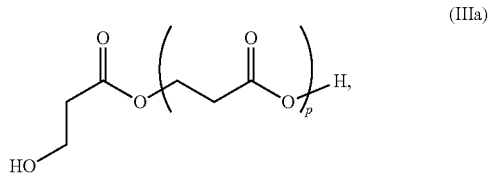

or a salt thereof, or a mixture of any two or more of these, where p is from 0 to 9. In certain embodiments p is from 0 to 5. In certain embodiments, p is 0, i.e., hydracrylic acid. In certain embodiments, p is 1. In certain embodiments, p is 2. In certain embodiments, p is 3. In certain embodiments, p is 4. In certain embodiments, p is 5. In certain embodiments, p is 6. In certain embodiments, p is 7. In certain embodiments, p is 8. In certain embodiments, p is 9. In certain embodiments, where the chain transfer agent of Formula (IIIa) is an oligomer, it is characterized in that it has a number average molecular weight of about 200 g/mol, about 300 g/mol, about 400 g/mol, about 500 g/mol, about 600 g/mol or about 700 g/mol, or is within a range bounded by any two of these values.

In certain embodiments, use of the chain transfer agent of Formula (IIIa), and incorporation of a hydracrylate end group onto many, most or substantially all chain ends, provides controlled production of the Polypropiolactone chains of Formula (II), having relatively short chain lengths and in compositions having lower PDI, which in turn allows for a more controlled pyrolysis of the PPL composition relative to PPL that substantially lacks hydracrylate end groups.

In certain embodiments, the chain transfer agent is hydracrylic acid or a salt thereof. In certain embodiments of the method, the chain transfer agent is hydracrylic acid dimer,

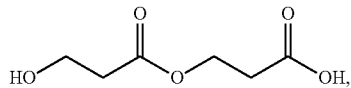

or a salt thereof. In certain embodiments of the method, the chain transfer agent is hydacrylic acid trimer,

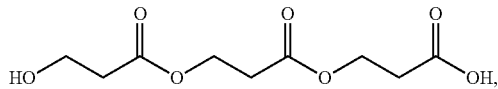 [SMILES: O=C(O)CCOC(=O)CCOC(=O)CCO]

or a salt thereof.

Polymerization Catalysts

In certain embodiments, the beta propiolactone is contacted with the chain transfer agent in the presence of a polymerization catalyst. A variety of catalysts may be used in the polymerization reaction, including by not limited to metals (e.g., lithium, sodium, potassium, magnesium, calcium, zinc, aluminum, titanium, cobalt, etc.) metal oxides, salts of alkali and alkaline earth metals (such as carbonates, borates, hydroxides, alkoxides, and carboxylates), and borates, silicates, or salts of other metals. In certain embodiments, suitable catalysts include carboxylate salts of metal ions. In certain embodiments suitable catalysts include carboxylate salts of organic cations. In some embodiments, a carboxylate salt is other than a carbonate. In some embodiments, a carboxylate salt is acrylate.

In certain embodiments, polymerizing the BPL to polypropiolactone polymers, or salts thereof, having acrylate or hydracrylate end groups, including polypropiolactone chains of Formula (I) and/or (II), is performed in the presence of a polymerization catalyst. In certain embodiments, suitable polymerization catalysts include carboxylate salts of metal ions or organic cations.

In certain embodiments, the polymerization catalyst is combined with BPL in a molar ratio from about 1:100,000 polymerization catalyst:BPL to about 1:10 polymerization catalyst:BPL. In certain embodiments the molar ratio of polymerization catalyst:BPL is about 1:100,000, 1:50,000, 1:20,000, 1:10,000, 1:5,000, 1:1,000, 1:500, 1:200, 1:100 or a range including any two of these ratios.

In certain embodiments, polymerizing the BPL to polypropiolactone polymers, or salts thereof, having acrylate or hydracrylate end groups, including polypropiolactone chains of Formula (I) and/or (II), is performed in the presence of a defined ratio of BPL:chain transfer agent: catalyst. In certain embodiments, the ratio employed is selected such that the amount of catalyst utilized is minimized while still achieving the desired PPL molecular weight and end-group composition. For example, when a catalyst used comprises an initiator group that does not lead to formation of a polymer chain of Formula (I) or (II), it is desirable to keep the ratio of CTA:catalyst high so as to minimize the proportion of polypropiolactone chains in the resulting PPL composition that do not conform to Formula (I) or (II). In addition, the molar ratio of BPL to the sum of the CTA and the catalyst will determine the value of n described in the Formula (I) or (II) therefore, this ratio is preferably maintained in the range of about 10:1 to about 1,000:1 to obtain PPL compositions having the molecular weight ranges described above and in the classes and subclasses herein.

In certain embodiments, polymerizing the BPL to polypropiolactone polymers, or salts thereof, having acrylate or hydracrylate end groups, including polypropiolactone chains of Formula (I) and/or (II), is performed under conditions such that the amount of BPL converted is from about 10 to about 1,000 times the amount of catalyst and CTA employed (on a molar basis). In certain embodiments, polymerizing the BPL to polypropiolactone polymers, or salts thereof, having acrylate or hydracrylate end groups, including polypropiolactone chains of Formula (I) and/or (II), is performed under conditions such that the molar ratio of BPL:(catalyst+CTA) is about 1,000:1, about 700:1, about 500:1, about 400:1, about 300:1, about 250:1, about 200:1, about 150:1, about 100:1, about 50:1, about 20:1 or about 10:1.

In certain embodiments, polymerizing the BPL to polypropiolactone polymers, or salts thereof, having acrylate or hydracrylate end groups, including polypropiolactone chains of Formula (I) and/or (II), is performed under conditions such that a molar amount of BPL converted to polymer is from 100 to about 100,000 times the molar amount of catalyst employed and from about 10 times to about 1,000 times the molar amount of CTA employed. In certain embodiments, polymerizing the BPL to polypropiolactone polymers, or salts thereof, having acrylate or hydracrylate end groups, including polypropiolactone chains of Formula (I) and/or (II), is performed under conditions such that molar ratios of BPL:CTA:catalyst range from about 100:10:1 to about 100,000:1,000:1. In certain embodiments, the BPL:CTA:catalyst ratio is about 100:10:1, about 200:10:1, about 500:10:1 or about 1,000:10:1. In certain embodiments, the BPL:CTA:catalyst ratio is about 500:50:1, about 1,000:50:1, about 2,500:50:1, about 5,000:50:1, or about 10,000:50:1. In certain embodiments, the BPL:CTA:catalyst ratio is about 1,000:100:1, about 2,000:100:1, about 5,000:100:1, about 10,000:100:1, about 50,000:100:1, or about 100,000:100:1. In certain embodiments, the BPL:CTA:catalyst ratio is about 2,000:200:1, about 5,000:200:1, about 10,000:200:1, about 50,000:200:1, or about 100,000:200:1. In certain embodiments, the BPL:CTA:catalyst ratio is about 5,000:500:1, about 10,000:500:1, about 25,000:500:1, about 50,000:500:1, or about 100,000:500:1. In certain embodiments, the BPL:CTA:catalyst ratio is about 10,000:1,000:1, about 20,000:1,000:1, about 50,000:1,000:1, or about 100,000:1,000:1.

In certain embodiments, the polymerization catalyst is combined with BPL in a molar ratio up to about 1:100,000 polymerization catalyst:BPL. In certain embodiments, the ratio is from about 1:100,000 to about 25:100 polymerization catalyst:BPL. In certain embodiments, the polymerization catalyst is combined with BPL in a molar ratio of about 1:50,000 polymerization catalyst:BPL to about 1:25,000 polymerization catalyst:BPL. In certain embodiments, the polymerization catalyst is combined with BPL in a molar ratio of about 1:25,000 polymerization catalyst:BPL to about 1:10,000 polymerization catalyst:BPL. In certain embodiments, the polymerization catalyst is combined with BPL in a molar ratio of about 1:20,000 polymerization catalyst:BPL to about 1:10,000 polymerization catalyst:BPL. In certain embodiments, the polymerization catalyst is combined with BPL in a molar ratio of about 1:15,000 polymerization catalyst:BPL to about 1:5,000 polymerization catalyst:BPL. In certain embodiments, the polymerization catalyst is combined with BPL in a molar ratio of about 1:5,000 polymerization catalyst:BPL to about 1:1,000 polymerization catalyst:BPL. In certain embodiments, the polymerization catalyst is combined with BPL in a molar ratio of about 1:2,000 polymerization catalyst:BPL to about 1:500 polymerization catalyst:BPL. In certain embodiments, the polymerization catalyst is combined with BPL in a molar ratio of about 1:1,000 polymerization catalyst:BPL to about 1:200 polymerization catalyst:BPL. In certain embodiments, the polymerization catalyst is combined with BPL in a molar ratio of about 1:500 polymerization catalyst:BPL to about 1:100 polymerization catalyst:BPL. In certain embodiments the molar ratio of polymerization catalyst:BPL is about 1:50,000, 1:25,000, 1:15,000, 1:10,000, 1:5,000, 1:1,000, 1:500, 1:250 or a range including any two of these values. In certain embodiments the molar ratio of polymerization catalyst:BPL is about 1:100, 5:100, 10:100, 15:100, 20:100, 25:100 or a range including any two of these values.

In certain embodiments, where the polymerization catalyst comprises a carboxylate salt, the carboxylate has a structure such that upon initiating polymerization of BPL, the polymer chains produced have an acrylate chain end. In certain embodiments, the carboxylate ion on a polymerization catalyst is the anionic form of the chain transfer agent used in the polymerization process. In one variation, acrylic acid and sodium acrylate are used in the methods described herein.

In certain embodiments, the carboxylate salt of the polymerization catalyst is an acrylate salt (i.e., the anionic form) of a compound of Formula (III):

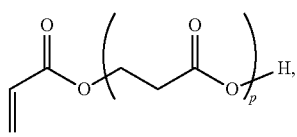

(III)

or a mixture of any two or more of these, where p is from 0 to 9. In certain embodiments, p is from 0 to 5. In certain embodiments, the carboxylate salt of the polymerization catalyst is an acrylate salt (i.e., of compound of Formula (III) where p=0).

In certain embodiments, the carboxylate salt of the polymerization catalyst is a salt of an acrylic acid dimer,

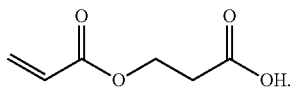

In certain embodiments, the carboxylate salt of the polymerization catalyst is a salt of an acrylic acid trimer,

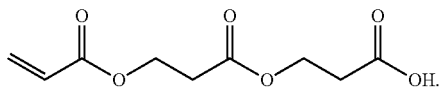

In certain embodiments, where the polymerization catalyst comprises a carboxylate salt, the carboxylate is the anionic form of a $C_{1-40}$ carboxylic acid. In certain embodiments, the carboxylate salt can be a salt of a polycarboxylic acid (e.g. a compound having two or more carboxylic acid groups). In certain embodiments, the carboxylate comprises the anion of a $C_{1-20}$ carboxylic acid. In certain embodiments, the carboxylate comprises the anion of a $C_{1-12}$ carboxylic acid. In certain embodiments, the carboxylate comprises the anion of a $C_{1-8}$ carboxylic acid. In certain embodiments, the carboxylate comprises the anion of a $C_{1-4}$ carboxylic acid. In certain embodiments, the carboxylate comprises the anion of an optionally substituted benzoic acid. In certain embodiments, the carboxylate is selected from the group consisting of: formate, acetate, propionate, valerate, butyrate, $C_{5-10}$ aliphatic carboxylate, and $C_{10-20}$ aliphatic carboxylate.

As noted, in certain embodiments, the polymerization catalyst comprises a carboxylate salt of an organic cation. In certain embodiments, the polymerization catalyst comprises a carboxylate salt of a cation wherein the positive charge is located at least partially on a nitrogen, sulfur, or phosphorus atom. In certain embodiments, the polymerization catalyst comprises a carboxylate salt of a nitrogen cation. In certain embodiments, the polymerization catalyst comprises a carboxylate salt of a cation selected from the group consisting of: ammonium, amidinium, guanidinium, a cationic form of a nitrogen heterocycle, and any combination of two or more of these. In certain embodiments, the polymerization catalyst comprises a carboxylate salt of a phosphorus cation. In certain embodiments, the polymerization catalyst comprises a carboxylate salt of a cation selected from the group consisting of: phosphonium and phosphazenium. In certain embodiments, the polymerization catalyst comprises a carboxylate salt of a sulfur-containing cation. In certain embodiments, the polymerization catalyst comprises a sulfonium salt.

In certain embodiments, the polymerization catalyst comprises a carboxylate salt of a metal. In certain embodiments, the polymerization catalyst comprises a carboxylate salt of a alkali or alkaline earth metal. In certain embodiments, the polymerization catalyst comprises a carboxylate salt of an alkali metal. In certain embodiments, the polymerization catalyst comprises a carboxylate salt of sodium or potassium. In certain embodiments, the polymerization catalyst comprises a carboxylate salt of sodium.

In certain embodiments, the polymerization catalyst comprises a carboxylate salt of a protonated amine:

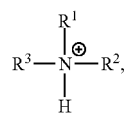

wherein:

each $R^1$ and $R^2$ is independently hydrogen or an optionally substituted radical selected from the group consisting of $C_{1-20}$ aliphatic; $C_{1-20}$ heteroaliphatic; a 3- to 8-membered saturated or partially unsaturated monocyclic carbocycle; a 7- to 14-membered saturated or partially unsaturated polycyclic carbocycle; a 5- to 6-membered monocyclic heteroaryl ring having 1-4 heteroatoms independently selected from nitrogen, oxygen, or sulfur; an 8- to 14-membered polycyclic heteroaryl ring having 1-5 heteroatoms independently selected from nitrogen, oxygen, or sulfur; a 3- to 8-membered saturated or partially unsaturated monocyclic heterocyclic ring having 1-3 heteroatoms independently selected from nitrogen, oxygen, or sulfur; a 6- to 14-membered saturated or partially unsaturated polycyclic heterocycle having 1-5 heteroatoms independently selected from nitrogen, oxygen, or sulfur; phenyl; or an 8- to 14-membered polycyclic aryl ring; wherein $R^1$ and $R^2$ can be taken together with intervening atoms to form one or more optionally substituted rings optionally containing one or more additional heteroatoms; and each $R^3$ is independently hydrogen or an optionally substituted radical selected from the group consisting of $C_{1-20}$ aliphatic; $C_{1-20}$ heteroaliphatic; a 3- to 8-membered saturated or partially unsaturated monocyclic carbocycle; a 7- to 14-membered saturated or partially unsaturated polycyclic carbocycle; a 5- to 6-membered monocyclic heteroaryl ring having 1-4 heteroatoms independently selected from nitrogen, oxygen, or sulfur; an 8- to 14-membered polycyclic heteroaryl ring having 1-5 heteroatoms independently selected from nitrogen, oxygen, or sulfur; a 3- to 8-membered saturated or partially unsaturated monocyclic heterocyclic ring having 1-3 heteroatoms independently selected from nitrogen, oxygen, or sulfur; a 6- to 14-membered saturated or partially unsaturated polycyclic heterocycle having 1-5 heteroatoms independently selected from nitrogen, oxygen, or sulfur; phenyl; or an 8- to 14-membered polycyclic aryl ring; wherein an $R^3$ group can be taken with an $R^1$ or $R^2$ group to form one or more optionally substituted rings.

In certain embodiments where the polymerization catalyst comprises a carboxylate salt of a protonated amine, the protonated amine is selected from the group consisting of:

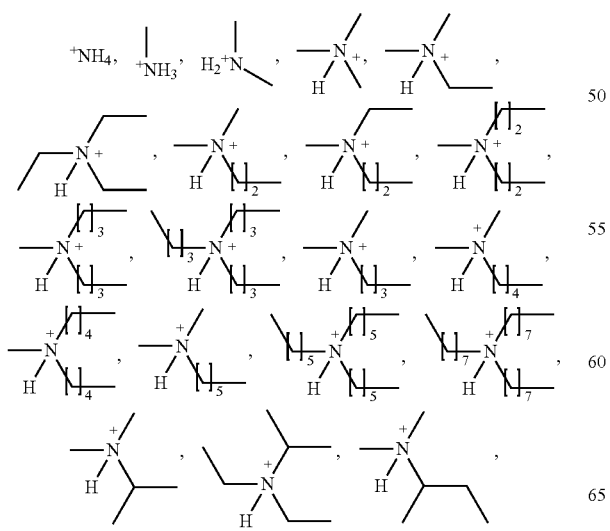

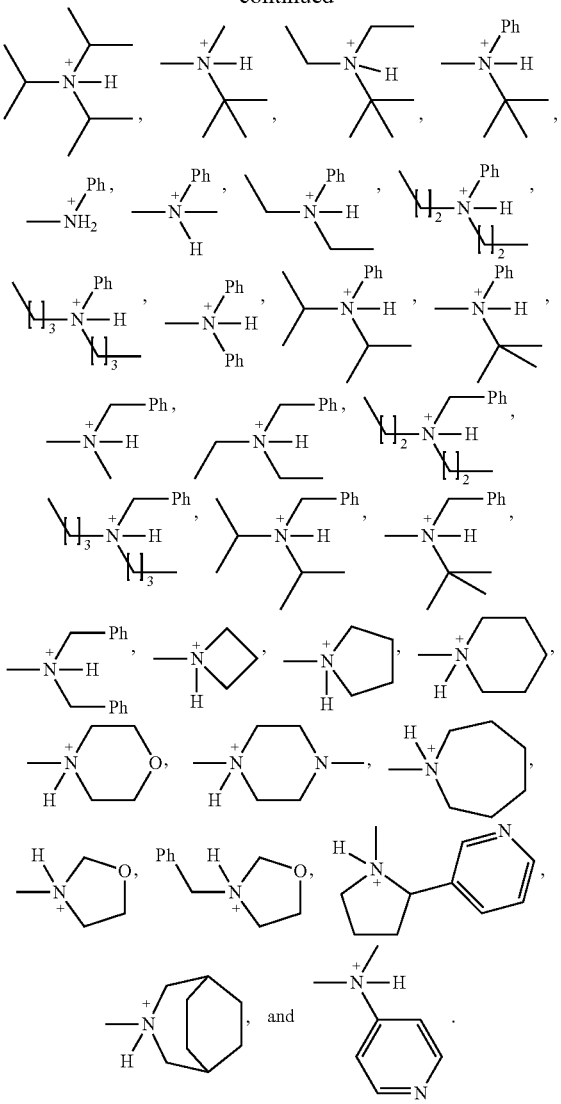

In certain embodiments, the polymerization catalyst comprises a carboxylate salt of a quaternary ammonium salt:

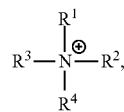

where:
each $R^1$, $R^2$ and $R^3$ is described above; and
each $R^4$ is independently hydrogen or an optionally substituted radical selected from the group consisting of $C_{1-20}$ aliphatic; $C_{1-20}$ heteroaliphatic; a 3- to 8-membered saturated or partially unsaturated monocyclic carbocycle; a 7- to 14-membered saturated or partially unsaturated polycyclic carbocycle; a 5- to 6-membered monocyclic heteroaryl ring having 1-4 heteroatoms independently selected from nitrogen, oxygen, or sulfur; an 8- to 14-membered polycyclic heteroaryl ring having 1-5 heteroatoms independently selected from nitrogen, oxygen, or sulfur; a 3- to 8-membered saturated or partially unsaturated monocyclic heterocyclic ring having 1-3 heteroatoms independently selected from nitrogen, oxygen, or sulfur; a 6- to 14-membered saturated or partially unsaturated polycyclic heterocycle having 1-5 heteroatoms independently selected from nitrogen, oxygen, or sulfur; phenyl; or an 8- to 14-membered polycyclic aryl ring; wherein an $R^4$ group can be taken with an $R^1$, $R^2$ or $R^3$ group to form one or more optionally substituted rings.

In certain embodiments, a polymerization catalyst comprises a carboxylate salt of a guanidinium group:

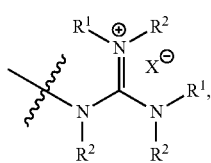

wherein each $R^1$ and $R^2$ is independently as defined above and described in classes and subclasses herein. In certain embodiments, each $R^1$ and $R^2$ is independently hydrogen or $C_{1-20}$ aliphatic. In certain embodiments, each $R^1$ and $R^2$ is independently hydrogen or $C_{1-12}$ aliphatic. In certain embodiments, each $R^1$ and $R^2$ is independently hydrogen or $C_{1-20}$ heteroaliphatic. In certain embodiments, each $R^1$ and $R^2$ is independently hydrogen or phenyl. In certain embodiments, each $R^1$ and $R^2$ is independently hydrogen or 8- to 10-membered aryl. In certain embodiments, each $R^1$ and $R^2$ is independently hydrogen or 5- to 10-membered heteroaryl. In certain embodiments, each $R^1$ and $R^2$ is independently hydrogen or 3- to 7-membered heterocyclic. In certain embodiments, one or more of $R^1$ and $R^2$ is optionally substituted $C_{1-12}$ aliphatic.

In certain embodiments, any two or more $R^1$ or $R^2$ groups are taken together with intervening atoms to form one or more optionally substituted carbocyclic, heterocyclic, aryl, or heteroaryl rings. In certain embodiments, $R^1$ and $R^2$ groups are taken together to form an optionally substituted 5- or 6-membered ring. In certain embodiments, three or more $R^1$ and/or $R^2$ groups are taken together to form an optionally substituted fused ring system.

In certain embodiments, an $R^1$ and $R^2$ group are taken together with intervening atoms to form a compound selected from:

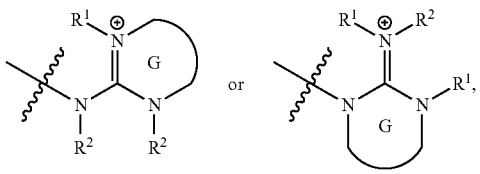

wherein each $R^1$ and $R^2$ is independently as defined above and described in classes and subclasses herein, and Ring G is an optionally substituted 5- to 7-membered saturated or partially unsaturated heterocyclic ring.

It will be appreciated that when a guanidinium cation is depicted as

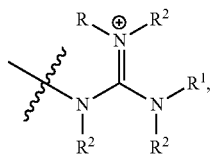

all such resonance forms are contemplated and encompassed by the present disclosure. For example, such groups can also be depicted as

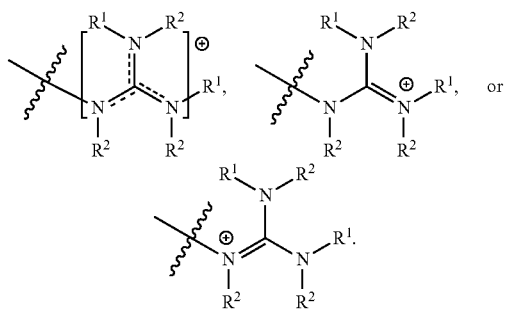

In specific embodiments, a guanidinium cation is selected from the group consisting of:

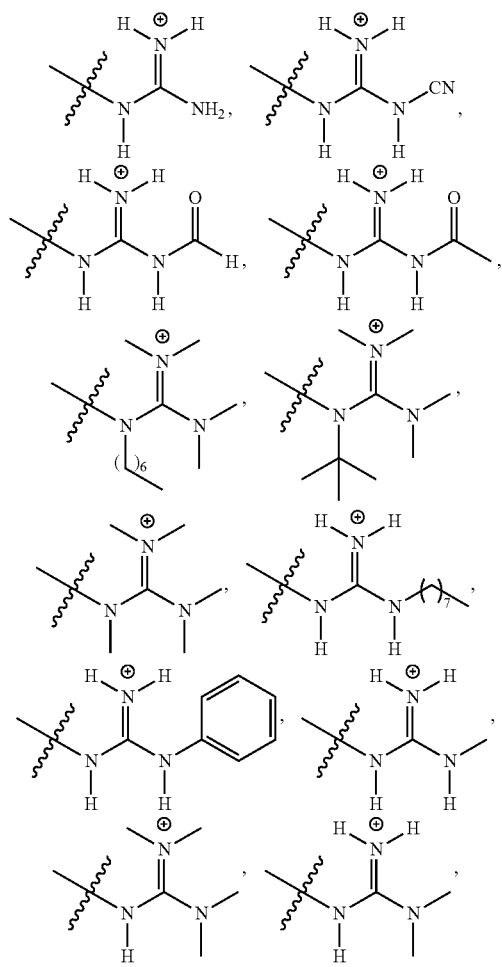

-continued

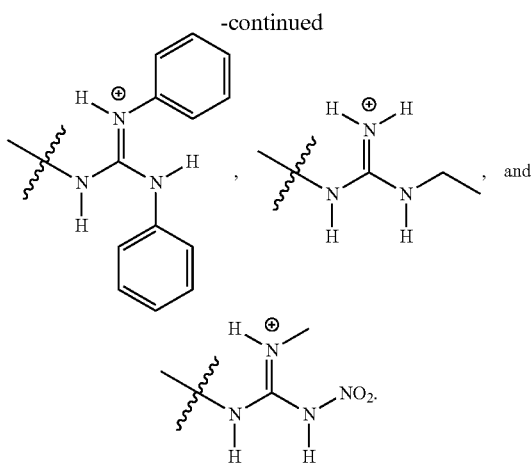

In certain embodiments, a polymerization catalyst comprises a carboxylate salt of a sulfonium group or an arsonium group, such as

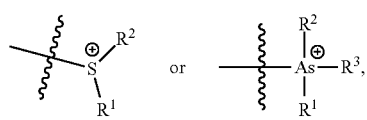

wherein each of $R^1$, $R^2$, and $R^3$ are as defined above and described in classes and subclasses herein.

In specific embodiments, an arsonium cation is selected from the group consisting of:

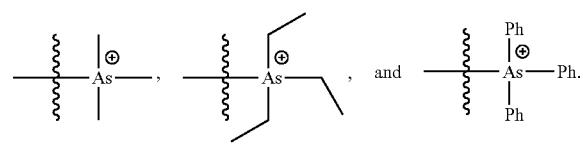

In certain embodiments, a polymerization catalyst comprises a carboxylate salt of an optionally substituted nitrogen-containing heterocycle. In certain embodiments, the nitrogen-containing heterocycle is an aromatic heterocycle. In certain embodiments, the optionally substituted nitrogen-containing heterocycle is selected from the group consisting of: pyridine, imidazole, pyrrolidine, pyrazole, quinoline, thiazole, dithiazole, oxazole, triazole, pyrazolem, isoxazole, isothiazole, tetrazole, pyrazine, thiazine, and triazine.

In certain embodiments, a nitrogen-containing heterocycle includes a quaternarized nitrogen atom. In certain embodiments, a nitrogen-containing heterocycle includes an iminium moiety such as

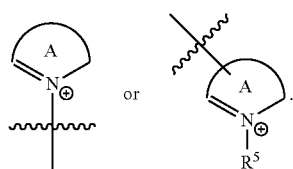

In certain embodiments, the optionally substituted nitrogen-containing heterocycle is selected from the group consisting of pyridinium, imidazolium, pyrrolidinium, pyrazolium, quinolinium, thiazolium, dithiazolium, oxazolium, triazolium, isoxazolium, isothiazolium, tetrazolium, pyrazinium, thiazinium, and triazinium.

In certain embodiments, a nitrogen-containing heterocycle is linked to a metal complex via a ring nitrogen atom. In certain embodiments, a ring nitrogen to which the attachment is made is thereby quaternized, and In certain embodiments, linkage to a metal complex takes the place of an N—H bond and the nitrogen atom thereby remains neutral. In certain embodiments, an optionally substituted N-linked nitrogen-containing heterocycle is a pyridinium derivative. In certain embodiments, optionally substituted N-linked nitrogen-containing heterocycle is an imidazolium derivative. In certain embodiments, optionally substituted N-linked nitrogen-containing heterocycle is a thiazolium derivative. In certain embodiments, optionally substituted N-linked nitrogen-containing heterocycle is a pyridinium derivative.

In certain embodiments, a polymerization catalyst comprises a carboxylate salt of

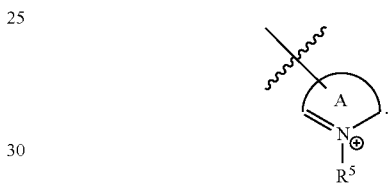

In certain embodiments, ring A is an optionally substituted, 5- to 10-membered heteroaryl group. In certain embodiments, Ring A is an optionally substituted, 6-membered heteroaryl group. In certain embodiments, Ring A is a ring of a fused heterocycle. In certain embodiments, Ring A is an optionally substituted pyridyl group.

In specific embodiments, a nitrogen-containing heterocyclic cation is selected from the group consisting of:

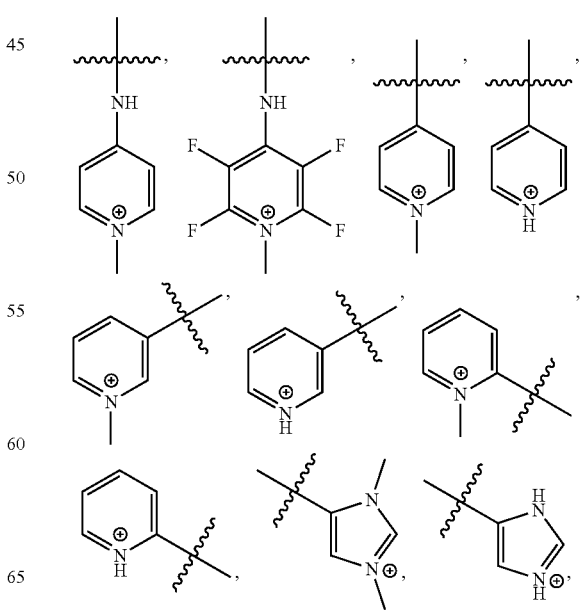

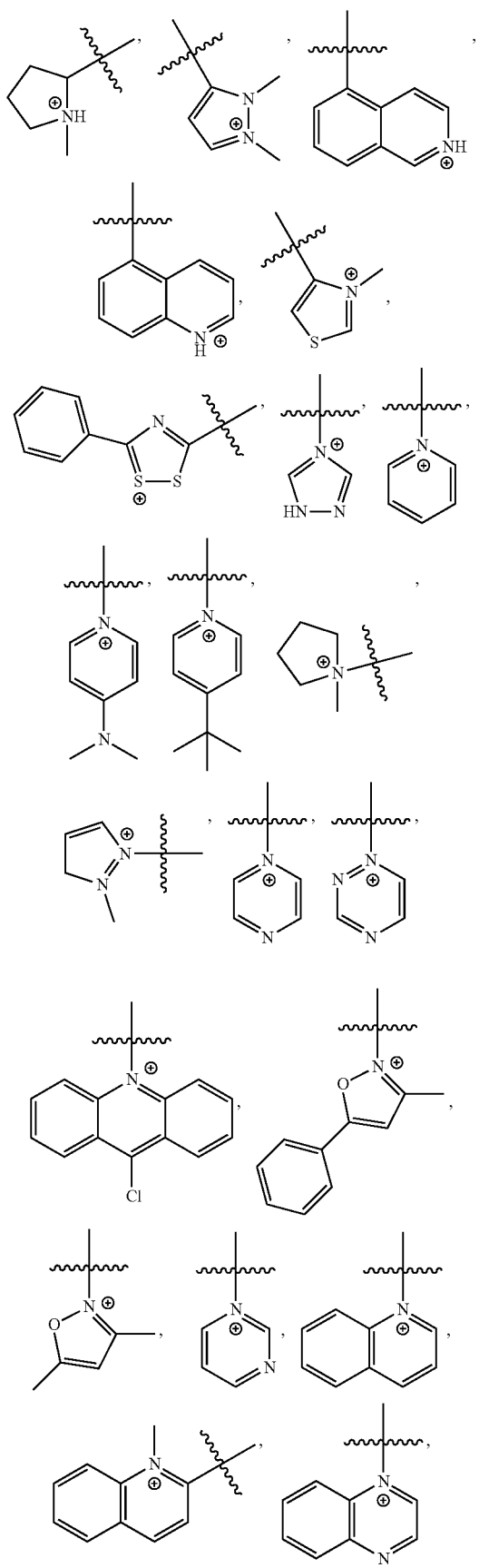

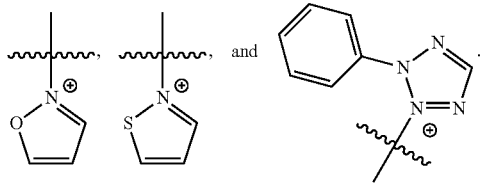

In certain embodiments, a polymerization catalyst comprises a carboxylate salt of

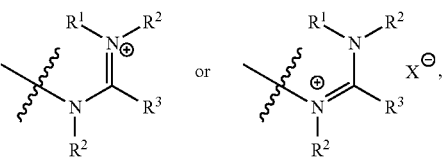

where each $R^1$, $R^2$, and $R^3$ is independently as defined above and described in classes and subclasses herein.

In certain embodiments, a polymerization catalyst comprises a carboxylate salt of

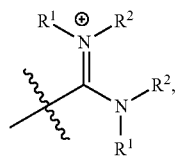

wherein each $R^1$ and $R^2$ is independently as defined above and described in classes and subclasses herein.

In certain embodiments, a polymerization catalyst comprises a carboxylate salt of

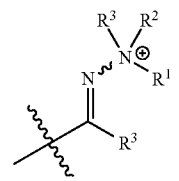

wherein each $R^1$, $R^2$, and $R^3$ is independently as defined above and described in classes and subclasses herein.

In certain embodiments, a polymerization catalyst comprises a carboxylate salt of

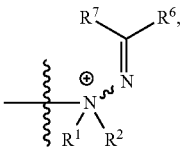

wherein each of $R^1$, $R^2$, $R^6$, and $R^7$ is as defined above and described in classes and subclasses herein.

In certain embodiments, $R^6$ and $R^7$ are each independently an optionally substituted group selected from the group consisting of $C_{1-20}$ aliphatic; $C_{1-20}$ heteroaliphatic; phenyl, and 8-10-membered aryl. In certain embodiments, $R^6$ and $R^7$ are each independently an optionally substituted $C_{1-20}$ aliphatic. In certain embodiments, $R^6$ and $R^7$ are each independently an optionally substituted $C_{1-20}$ heteroaliphatic having. In certain embodiments, $R^6$ and $R^7$ are each independently an optionally substituted phenyl or 8-10-membered aryl. In certain embodiments, $R^6$ and $R^7$ are each independently an optionally substituted 5- to 10-membered heteroaryl. In certain embodiments, $R^6$ and $R^7$ can be taken together with intervening atoms to form one or more rings selected from the group consisting of: optionally substituted $C_3$-$C_{14}$ carbocycle, optionally substituted $C_3$-$C_{14}$ heterocycle, optionally substituted $C_6$-$C_{10}$ aryl, and optionally substituted 5- to 10-membered heteroaryl. In certain embodiments, $R^6$ and $R^7$ are each independently an optionally substituted $C_{1-6}$ aliphatic. In certain embodiments, each occurrence of $R^6$ and $R^7$ is independently methyl, ethyl, propyl, butyl, pentyl, hexyl, heptyl, octyl, or benzyl. In certain embodiments, each occurrence of $R^6$ and $R^7$ is independently perfluoro. In certain embodiments, each occurrence of $R^6$ and $R^7$ is independently —$CF_2CF_3$.

In certain embodiments, a polymerization catalyst comprises a carboxylate salt of

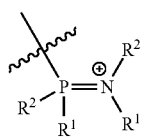

wherein each $R^1$ and $R^2$ is independently as defined above and described in classes and subclasses herein.

In certain embodiments, a polymerization catalyst comprises a carboxylate salt of

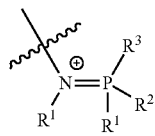

wherein each $R^1$, $R^2$, and $R^3$ is independently as defined above and described in classes and subclasses herein.

In certain embodiments, a cation is

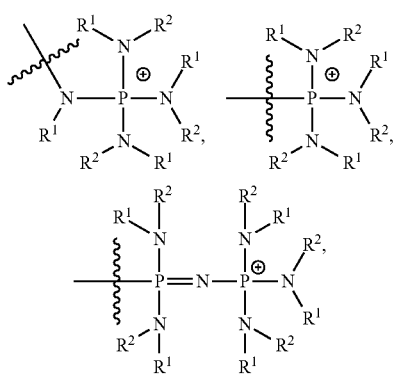

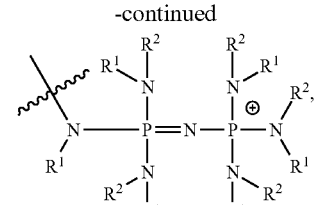

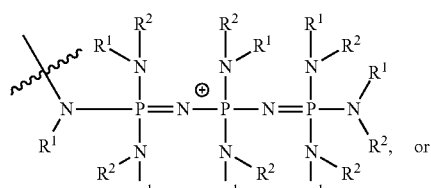

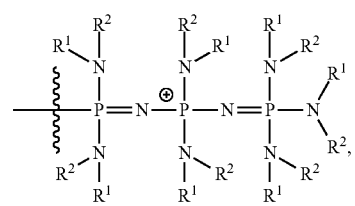

wherein each $R^1$ and $R^2$ is independently as defined above and described in classes and subclasses herein.

In certain embodiments, a polymerization catalyst comprises a carboxylate salt of

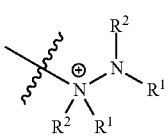

wherein each $R^1$ and $R^2$ is independently as defined above and described in classes and subclasses herein.

In certain embodiments, a polymerization catalyst comprises a carboxylate salt of

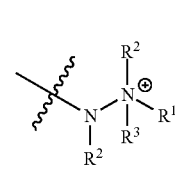

wherein each $R^1$, $R^2$, and $R^3$ is independently as defined above and described in classes and subclasses herein.

In certain embodiments, a polymerization catalyst comprises a carboxylate salt of

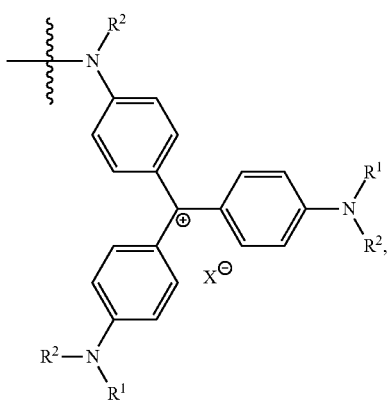

wherein each $R^1$ and $R^2$ is independently as defined above and described in classes and subclasses herein. In certain embodiments, suitable catalysts include transition metal compounds. In certain embodiments, suitable catalysts include acid catalysts. In certain embodiments, the catalyst is a heterogeneous catalyst.

In certain embodiments, any of the foregoing cationic functional groups are attached to a solid support. Examples of suitable solid supports include polymeric solids (e.g. polymer beads, films, fibers, fabric, particles and the like) as well as inorganic solids (e.g. clays, silicas, aluminas, diatomaceous earth, ceramics, metal oxides, mineral fibers beads or particles, and the like). Specific examples of such supported cationic functional groups include polystyrene resin beads functionalized with ammonium groups, polystyrene resin beads functionalized with phosphonium groups, and polystyrene resin beads functionalized with guanidinium groups. Specific examples of such supported cationic functional groups include silica particles functionalized with ammonium groups, alumina particles functionalized with phosphonium groups, and ceramic beads functionalized with guanidinium groups. In certain embodiments, polymerization catalysts comprise carboxylate salts of any of the foregoing supported solid cationic functional groups. In certain embodiments, polymerization catalysts comprise acrylate salts of any of the foregoing supported solid cationic functional groups.

In certain embodiments, polymerization catalysts comprise cationic solids wherein the cations comprise metal atoms. In certain embodiments, polymerization catalysts comprise carboxylate salts of any of the foregoing supported solid cationic metal atoms. In certain embodiments, polymerization catalysts comprise acrylate salts of any of the foregoing supported solid cationic metal atoms.

Methods for Preparing Acrylic Acid from the PPL Compositions Containing Polypropiolactone Chains of Formula (I) and/or (II)

In other aspects, provided is a method for producing acrylic acid, comprising heating any of the polypropiolactone compositions described herein to produce the acrylic acid. For example, in some variations, the polypropiolactone composition comprises polypropiolactone polymers, or salts thereof, independently comprising:

(a) an acrylate end group having the structure

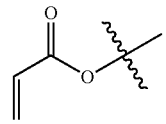 [SMILES: *OC(=O)C=C]

or a hydracrylate end group having the structure

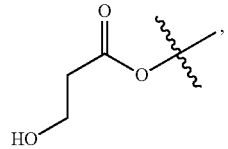

and
(b) a polymer chain comprising repeating units having the structure

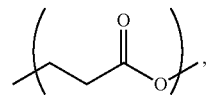

wherein the acrylate end group or the hydracrylate end group caps the alkyl terminus of the polymer chain.

In certain variations of the foregoing, (i) the polypropiolactone polymers, or salts thereof, have an $M_n$ of less than or equal to about 40,000 g/mol; (ii) the polypropiolactone composition has a polydispersity of less than or equal to about 2.0; or (iii) at least 90 wt % of the polypropiolactone polymers, or salts thereof, in the polypropiolactone composition have the acrylate end group or the hydracrylate end group, or any combination of (i)-(iii). The resulting acrylic acid produced from such method has a high degree of purity.

In another aspect, a method is provided for producing acrylic acid, the method comprising heating (e.g., pyrolyzing) a polypropiolactone (PPL) composition containing polypropiolactone chains of Formula (I):

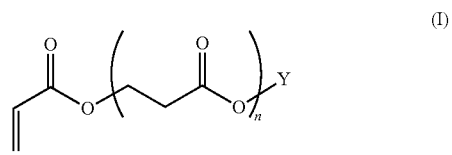

where n is an integer from 10 to about 1,000 and Y is either —H or a cation, to liberate acrylic acid.

In another aspect, a method is provided for producing acrylic acid, the method comprising heating a PPL composition containing polypropiolactone chains of Formula (II):

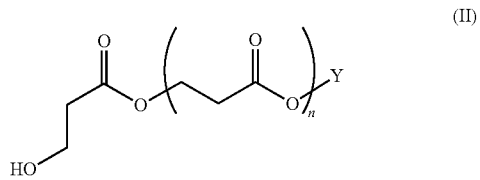

where n is an integer from 10 to about 1,000 and Y is either —H or a cation, to liberate acrylic acid.

In some embodiments, the PPL compositions include (e.g., at least about 30 wt %, 40 wt %, 50 wt %, 60 wt %, 70 wt %, 80 wt %, 90 wt %) of the Polypropiolactone chains of Formula (I) or (II) relative to Polypropiolactone chains without acrylate or hydracrylate end groups.

Upon pyrolysis, the acrylate end group of (I) serves to liberate one mole of acrylic acid, whereas the hydroxyl group of (II) serves to liberate one mole of water plus one mole of acrylic acid. Thus, Polypropiolactone chains of Formula (II) are especially suitable for the preparation of highly pure forms of aqueous or water-containing acrylic acid (e.g., acrylic acid comprising 0.1%, 1%, 5%, 10%, 25%, 50%, 99% water, or a range including any two of these values). In certain embodiments, these forms of aqueous or water-containing acrylic acid are otherwise highly pure, meaning that they have less than (5%, 4%, 3%, 2%, 1%, 0.5%, 0.1%. 0.01%, 0.001% impurities, or a range including any two of these values), where the impurities include aldehyde impurities, products or byproducts of propylene oxidation, and/or stabilizers as defined herein, etc.

In certain embodiments, methods for preparing acrylic acid, such as crude and/or glacial acrylic acid, comprise the pyrolysis of any of the Polypropiolactone chains of Formula (I) and/or (II) described herein, or PPL compositions comprising the same. Acrylate and hydroxyl end groups of the polypropiolactone chains of Formula (I) and/or (II) were found to improve pyrolysis to acrylic acid, as either end group efficiently converts to acrylic acid or acrylic acid and water, respectively.

In certain embodiments, a method is provided for the production (e.g., integrated production) of a composition comprising polypropiolactone chains of Formula (I):

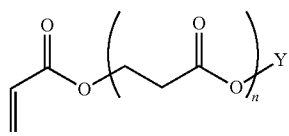

(I)

where n is an integer from 10 to about 1,000 and Y is either —H or a cation,
comprising polymerizing beta propiolactone in the presence of a chain transfer agent selected from the group consisting of: a compound of Formula (III):

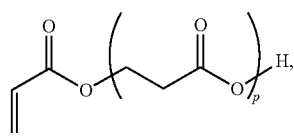

(III)

or a salt thereof, or a mixture of any two or more of these, where p is from 0 to 9. In certain embodiments, the composition further comprises polypropiolactone.

In certain embodiments, the beta propiolactone is contacted with the chain transfer agent in the presence of a polymerization catalyst. In certain embodiments, the polymerization catalyst is selected from the group consisting of:
a) an acrylate salt of a metal cation,
b) an acrylate salt of an organic cation,
c) a transition metal compound,
d) an acid catalyst, and
e) a base catalyst.

Any combinations of the polymerization catalysts described herein may also be used.

In certain embodiments, the beta propiolactone is contacted with the chain transfer agent at a temperature greater than 50° C. In certain embodiments, the temperature is in the range from 50° C. to about 250° C., or in the range from 80° C. to about 200° C., the range from 80° C. to about 180° C., or in the range from 100° C. to about 200° C., or in the range from 120° C. to about 180° C., or in the range from 140° C. to about 160° C.

In certain embodiments, the polypropiolactone composition formed is characterized in that at least 90%, 95%, 99%, 99.5%, 99.8 or 99.9% of the polymer chains in the composition have an acrylate end group.

In certain embodiments, the polypropiolactone composition formed is characterized in that at least 90%, 95%, 99%, 99.5%, 99.8 or 99.9% of the polymer chains in the composition are of Formula (I).

In certain embodiments, n is, on average in the polypropiolactone composition:
between 10 and 50, or
between 50 and 100, or
between 100 and 150, or
between 150 and 250, or
between 250 and 350, or
between 350 and 500.

In certain embodiments, the polypropiolactone composition is characterized in that it has a polydispersity index (PDI) of less than 2.

In certain embodiments, the polypropiolactone composition is characterized in that it has a PDI less than 1.8, or less than 1.6, or less than 1.5, or less than 1.3, or less than 1.2, or less than 1.1.

In certain embodiments, pyrolyzing the PPL composition containing polypropiolactone chains of Formula (I) and/or (II) is performed continuously (e.g., in a fed batch reactor or other continuous flow reactor format). In certain embodiments, the continuous pyrolysis process is linked to a continuous acrylic acid polymerization process (e.g. a polymerization process producing SAP or another AA polymerization product) to yield AA at a rate matched to the consumption rate of the AA polymerization process.

In certain embodiments, this method has the advantage of not requiring the addition and/or removal of stabilizers to or from the acrylic acid feed to the acrylic acid polymerization process. Thus, in certain variations, no stabilizer is used.

BPL Conversion to the Polypropiolactone Chains of Formula (I) and/or (II)

A beta-lactone feedstock stream used in accordance with provided methods and systems may be provided from any one or more of a number of known sources of BPL. Methods of making BPL are known in the art and include those described in U.S. Pat. Nos. 6,852,865, 8,445,703, 8,796,475, WO 2004089923 and WO 2013126375. In some embodiments, a feedstock stream comprising BPL enters a reaction zone described herein as a gas or as a liquid. The conversion of BPL to polypropiolactone polymers, or salts thereof, having acrylate or hydracrylate end groups, including polypropiolactone chains of Formula (I) and/or (II), may be performed in either the gas phase or the liquid phase and may be performed neat, or in the presence of a carrier gas, solvent, or other diluent. In some embodiments, a BPL feedstock stream is neat.

It will be appreciated that in certain embodiments, the methods and systems can also be directly integrated to the formation of ethylene oxide, thus avoiding the isolation and storage of this toxic and potentially explosive intermediate. In certain embodiments, the processes are fed by ethylene gas which is converted to ethylene oxide, the ethylene oxide then feeds a second reaction where carbonylation takes place to yield a feedstock stream comprising BPL.

In certain embodiments, conversion of BPL to polypropiolactone polymers, or salts thereof, having acrylate or hydracrylate end groups, including polypropiolactone chains of Formula (I) and/or (II), is performed in a continuous flow format. In certain embodiments, conversion of BPL to polypropiolactone polymers, or salts thereof, having acrylate or hydracrylate end groups, including polypropiolactone chains of Formula (I) and/or (II), is performed in a continuous flow format in the gas phase. In certain embodiments, conversion of BPL to polypropiolactone polymers, or salts thereof, having acrylate or hydracrylate end groups, including polypropiolactone chains of Formula (I) and/or (II), is performed in a continuous flow format in the liquid phase. In certain embodiments, conversion of BPL to polypropiolactone polymers, or salts thereof, having acrylate or hydracrylate end groups, including polypropiolactone chains of Formula (I) and/or (II), is performed in a liquid phase in a batch or semi-batch format. Conversion of BPL to polypropiolactone polymers, or salts thereof, having acrylate or hydracrylate end groups, including polypropiolactone chains of Formula (I) and/or (II), may be performed under a variety of conditions. In certain embodiments, the reaction may be performed in the presence of one or more acrylate catalysts that facilitate the transformation of the BPL to polypropiolactone polymers, or salts thereof, having acrylate or hydracrylate end groups, including polypropiolactone chains of Formula (I) and/or (II).

In certain embodiments, a feedstock stream comprising BPL is directed to a reaction stream in a reaction zone where it is contacted with a suitable acrylate catalyst and where at least a portion of the BPL is converted to polypropiolactone polymers, or salts thereof, having acrylate or hydracrylate end groups, including polypropiolactone chains of Formula (I) and/or (II). In some embodiments, the reaction zone is maintained at a temperature suitable for the formation of polypropiolactone polymers, or salts thereof, having acrylate or hydracrylate end groups, including polypropiolactone chains of Formula (I) and/or (II). In some embodiments, such temperature maintenance comprises the removal of heat from the reaction zone.

In some embodiments, a feedstock stream comprising BPL is directed to a reaction stream in a first reaction zone where it is contacted with a suitable acrylate catalyst and where at least a portion of the BPL is converted to a product stream containing polypropiolactone polymers, or salts thereof, having acrylate or hydracrylate end groups, including polypropiolactone chains of Formula (I) and/or (II). In some embodiments, the first reaction zone is maintained at a temperature suitable for the formation of polypropiolactone polymers, or salts thereof, having acrylate or hydracrylate end groups, including polypropiolactone chains of Formula (I) and/or (II). In some embodiments, such temperature maintenance comprises the removal of heat from the first reaction zone.

In certain embodiments, conversion of BPL to polypropiolactone polymers, or salts thereof, having acrylate or hydracrylate end groups, including polypropiolactone chains of Formula (I) and/or (II) utilizes a solid acrylate catalyst and the conversion is conducted at least partially in the gas phase. In certain embodiments, the solid acrylate catalyst in the beta lactone conversion stage comprises a solid acrylic acid catalyst. In certain embodiments, BPL is introduced as a liquid and contacted with a solid acrylate catalyst to form polypropiolactone chains of Formula (I) and/or (II), which undergoes pyrolysis to acrylic acid which is removed as a gaseous stream. In other embodiments, BPL is introduced as a gas, contacted with a solid acrylate catalyst to form polypropiolactone polymers, or salts thereof, having acrylate or hydracrylate end groups, including polypropiolactone chains of Formula (I) and/or (II), which undergoes pyrolysis to acrylic acid which is removed as a gaseous stream.

In certain embodiments, processes described herein are characterized in that the feed rates, reaction rates, and reactor sizes are scaled such that each subsequent stage in the process can utilize essentially all of the effluent from the previous stage. In certain embodiments, methods include one or more steps of modulating one or more system parameters selected from the group consisting of: the temperature and/or pressure of the lactone conversion stage, the temperature and/or pressure of the pyrolysis stage, and a combination of any two or more of these parameters. In certain embodiments, this modulation of system parameters is performed such that the conversion rate per unit time of each stage matches that of the previous stage so that the effluent of the previous stage may be used directly to feed the subsequent stage. In certain embodiments, methods include one or more steps of analyzing the effluent from one or more stages to assess its content. In certain embodiments, such analyzing steps include performing spectroscopy (e.g., infrared spectroscopy, nuclear magnetic resonance spectroscopy, ultraviolet or visible light spectroscopy and the like), chromatography (e.g., gas or liquid chromatography). In certain embodiments, such analyses are performed in a flow-through or stop-flow mode that provides real-time data on the chemical composition of the effluent. In certain embodiments, such data are used to provide a prompt to adjust one or more of the system parameters described above.

Pyrolysis of Polypropiolactone Chains of Formula (I) and/or (II)

In one aspect, BPL is converted to GAA without isolation of the intermediate PPL compositions containing the polypropiolactone polymers, or salts thereof, having acrylate or hydracrylate end groups, including chains of Formula (I) and/or (II). In some embodiments, polypropiolactone polymers, or salts thereof, having acrylate or hydracrylate end groups, including the polypropiolactone chains of Formula (I) and/or (II), formed by polymerization of BPL, in the presence of a chain-transfer reagent are concurrently converted to acrylic acid (e.g., GAA) via pyrolysis in the same reaction zone (e.g., a "one-pot" method). In some embodiments, the reaction zone supporting the reaction of BPL to polypropiolactone polymers, or salts thereof, having acrylate or hydracrylate end groups, including polypropiolactone chains of Formula (I) and/or (II), is maintained at a temperature at or above the pyrolysis temperature of polypropiolactone polymers, or salts thereof, having acrylate or hydracrylate end groups, including polypropiolactone chains of Formula (I) and/or (II), such that thermal decomposition of the same produces acrylic acid. Without wishing to be bound by any particular theory, it is believed that in such embodiments as BPL reacts with acrylic acid to start polymer chains, thermal decomposition may degrade the polymer to acrylic acid.

In certain embodiments, a PPL composition containing polypropiolactone polymers, or salts thereof, having acrylate or hydracrylate end groups, including chains of Formula (I) and/or (II), product stream is formed in a first reaction zone and then directed to a second reaction zone, wherein the second reaction zone is maintained at a temperature at or above the pyrolysis temperature of the polypropiolactone polymers, or salts thereof, having acrylate or hydracrylate end groups, including polypropiolactone chains of Formula (I) and/or (II), such that the thermal decomposition of the polypropiolactone polymers, or salts thereof, having acrylate or hydracrylate end groups, including polypropiolactone chains of Formula (I) and/or (II), produces acrylic acid. In some embodiments, the temperature of the first reaction zone is different than the temperature of the second reaction zone. In some embodiments, the temperature of the first reaction zone is below the pyrolysis temperature of the polypropiolactone polymers, or salts thereof, having acrylate or hydracrylate end groups, including polypropiolactone chains of Formula (I) and/or (II). Such embodiments may also be described as a "two-step" method, wherein at least a portion of BPL is converted to polypropiolactone polymers, or salts thereof, having acrylate or hydracrylate end groups, including polypropiolactone chains of Formula (I) and/or (II), prior to entering a reaction zone maintained at or above the pyrolysis temperature. In some embodiments, the PPL composition entering the second reaction zone contains an amount of unreacted BPL. In other words, the formation of polypropiolactone polymers, or salts thereof, having acrylate or hydracrylate end groups, including polypropiolactone chains of Formula (I) and/or (II), need not be complete prior to the PPL composition entering the second reaction zone. In such cases, BPL may undergo polymerization to polypropiolactone polymers, or salts thereof, having acrylate or hydracrylate end groups, including polypropiolactone chains of Formula (I) and/or (II), followed by pyrolysis within the second reaction zone.

It should generally be understood that reference to "a first reaction zone" and "a second reaction zone", etc. or "a first reactor" or "a second reactor", etc., does not necessarily imply an order of the reaction zones or reactors. In some variations, the use of such references denotes the number of reaction zones or reactors present. In other variations, an order may be implied by the context in which the reaction zones or reactors are configured or used.

Superabsorbent Polymers and Articles

In yet another aspect, provided is a superabsorbent polymer, comprising a polyacrylic acid that is derived, at least in part, from acrylic acid that derives from polypropiolactone polymers, or salts thereof, having acrylate or hydracrylate end groups, including polypropiolactone chains of Formula (I) and/or (II), as described herein.

In certain embodiments, provided is a superabsorbent polymer comprising polyacrylic acid that is derived from acrylic acid formed from the pyrolysis of a polypropiolactone chain of Formula (I):

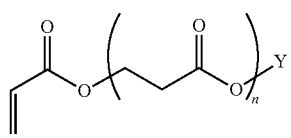

wherein n is an integer from 10 to about 1,000 and Y is —H or a cation, and wherein the superabsorbent polymer comprises less than about 1000 parts per million residual monoethylenically unsaturated monomer, and is substantially free of an aldehyde impurity or a compound that derives from the oxidation of propylene.

Monomeric GAA precursors of SAPs typically need to react to completion or nearly so to prevent or minimize the presence of residual unreacted monomer in the SAP or products, such as diapers, made from the SAP. Disclosed acrylic acid and polyacrylic acids made from the polypropiolactone polymers, or salts thereof, having acrylate or hydracrylate end groups, including polypropiolactone chains of Formula (I) or (II) described herein, are substantially free from compounds that derives from the oxidation of propylene and/or aldehyde impurities. As such, the disclosed acrylic acid reacts more fully to produce polyacrylic acid, sodium polyacrylate and other co-polymers, having minimal or substantially no residual unreacted acrylic acid, suitable for incorporated into SAPs.

Superabsorbent polymers are generally made from the polymerization of acrylic acid blended with sodium hydroxide in the presence of a radical initiator (e.g., azobisisobutyronitrile, AIBN) to form a polyacrylic acid sodium salt (sometimes referred to as sodium polyacrylate). This polymer is presently among the most common types of SAPs. Other materials are also used to make a superabsorbent polymer, such as polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile, among others. Superabsorbent polymers are generally made using one of three methods: gel polymerization, suspension polymerization or solution polymerization.

In certain embodiments, superabsorbent polymers prepared from polyacrylic acid, sodium polyacrylate, and acrylic acids that derive from the polypropiolactone polymers, or salts thereof, having acrylate or hydracrylate end groups, including polypropiolactone chains of Formula (I) or (II) described herein, have less than about 1000, 500, 200, 100, 50 or 10 parts per million residual monoethylenically unsaturated monomer, which for example may derive from an unsaturated acrylic acid monomer. In certain embodiments, the superabsorbent polymer is substantially free from a compound that derives from the oxidation of propylene. In certain embodiments, the superabsorbent polymer comprises less than about 1000, 500, 200, 100, 50 or 10 parts per million of the compound that derives from the oxidation of propylene. In certain embodiments, the superabsorbent polymer is substantially free from an aldehyde impurity. In certain embodiments, the superabsorbent polymer comprises less than about 1000, 500, 200, 100, 50 or 10 parts per million of the aldehyde impurity.

In another aspect, an article is provided comprising any of the superabsorbent polymers disclosed herein. In certain embodiments, the article is a disposable diaper, training pants, adult incontinence undergarment or sanitary napkin. In certain embodiments, the article is a disposable diaper.

ENUMERATED EMBODIMENTS

The following enumerated embodiments are representative of some aspects of the invention.

1. A method for the production of a polypropiolactone composition comprising polypropiolactone chains of Formula (I):

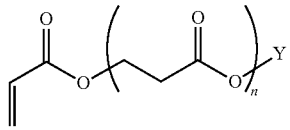

where n is an integer from 10 to about 1,000 and Y is either —H or a cation, comprising the step of polymerizing beta propiolactone in the presence of a chain transfer agent of Formula (III):

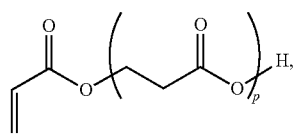

or a salt thereof, or a mixture of any two or more of these, where p is from 0 to 9.

2. The method of embodiment 1, wherein the beta propiolactone is contacted with the chain transfer agent in the presence of a polymerization catalyst.

3. The method of embodiment 2, wherein the polymerization catalyst is selected from the group consisting of:
   a) an acrylate salt of a metal cation,
   b) an acrylate salt of an organic cation,
   c) a transition metal compound,
   d) an acid catalyst, and
   e) a base catalyst.

4. The method of embodiment 1, wherein the beta propiolactone is contacted with the chain transfer agent at a temperature greater than 50° C.

5. The method of embodiment 4, wherein the temperature is in the range from 50° C. to about 250° C.

6. The method of embodiment 1, wherein at least 90% of polymer chains in the composition have an acrylate end group.

7. The method of embodiment 1, wherein at least 90% of polymer chains in the composition are the polypropiolactone chain of Formula (I).

8. The method of embodiment 1, wherein the composition has a polydispersity index (PDI) of less than 2.

9. A method for the production of acrylic acid comprising heating a polypropiolactone chain of Formula (I):

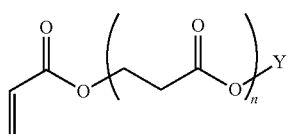

where n is an integer from 10 to about 1,000 and Y is either —H or a cation.

10. A polypropiolactone composition comprising polypropiolactone chains of Formula (I)

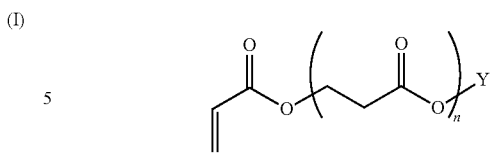

where n is an integer from 10 to about 1,000 and Y is either —H or a cation, and at least 90% of polymer chains in the composition are of formula (I).

11. The composition of embodiment 10, wherein the composition has a polydispersity index (PDI) of less than 2.

12. A reaction stream comprising polypropiolactone chains of Formula (I):

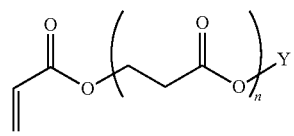

wherein n is an integer from 10 to about 1,000 and Y is either —H or a cation, and wherein the reaction stream produces acrylic acid at a rate of at least about 500 kg/hr.

13. A superabsorbent polymer comprising polyacrylic acid that derives from acrylic acid formed from the pyrolysis of a polypropiolactone chain of Formula (I):

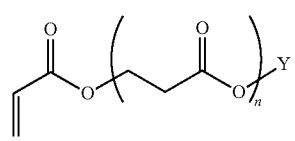

wherein n is an integer from 10 to about 1,000 and Y is either —H or a cation, and wherein the superabsorbent polymer comprises less than about 1000 parts per million residual monoethylenically unsaturated monomer, and is substantially free of an aldehyde impurity or a compound that derives from the oxidation of propylene.

14. An article comprising the superabsorbent polymer of embodiment 13.

15. The article of embodiment 14, wherein the article is a disposable diaper.

16. A method for producing a polypropiolactone composition, comprising: combining beta propiolactone and at least one compound of Formula (III), or a salt thereof, to produce the polypropiolactone composition, wherein:

the at least one compound of Formula (III) independently has the structure:

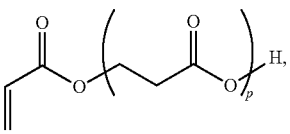

wherein each p is independently an integer from 0 to 9; and
the polypropiolactone composition comprises polypropiolactone polymers, or salts thereof, independently comprising:
(a) an acrylate end group having the structure

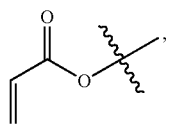

and
(b) a polymer chain comprising repeating units having the structure

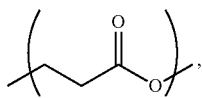

wherein the acrylate end group caps the alkyl terminus of the polymer chain, and
wherein:
(1) the polypropiolactone composition has an $M_n$ less than or equal to about 40,000 g/mol; or
(2) the polypropiolactone composition has a polydispersity less than or equal to about 2.0; or
(3) at least 90 wt % of the polypropiolactone composition comprises polypropiolactone polymers, or salts thereof, having the acrylate end group, or
any combinations of (1)-(3).
17. The method of embodiment 16, wherein the polypropiolactone polymers, or salts thereof, independently have a structure of Formula (I):

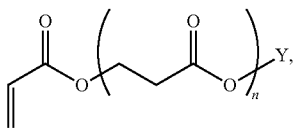

wherein:
n is an integer from 10 to 1,000; and
Y is —H or a cation.
18. The method of embodiment 16 or 17, wherein the beta propiolactone and the at least one compound of Formula (III), or a salt thereof, are further combined with a polymerization catalyst.
19. The method of embodiment 18, wherein the polymerization catalyst is selected from the group consisting of:
a) an acrylate salt of a metal cation,
b) an acrylate salt of an organic cation,
c) a transition metal compound,
d) an acid catalyst, and
e) a base catalyst,
or any combinations thereof.
20. The method of any one of embodiments 16 to 19, wherein the beta propiolactone is combined with the at least one compound of Formula (III), or a salt thereof, at a temperature greater than 50° C.
21. The method of embodiment 20, wherein the temperature is in the range from 140° C. to 200° C.

22. The method of any one of embodiments 16 to 21, at least 95 wt %, at least 96 wt %, at least 97 wt %, at least 98 wt %, at least 99 wt %, at least 99.1%, at least 99.2 wt %, at least 99.3 wt %, at least 99.4 wt %, at least 99.5 wt %, at least 99.6 wt %, at least 99.7 wt %, at least 99.8 wt %, or at least 99.9 wt %, of the polypropiolactone composition comprises polypropiolactone polymers, or salts thereof, having the acrylate end group.
23. The method of any one of embodiments 17 to 22, wherein at least 95 wt %, at least 96 wt %, at least 97 wt %, at least 98 wt %, at least 99 wt %, at least 99.1%, at least 99.2 wt %, at least 99.3 wt %, at least 99.4 wt %, at least 99.5 wt %, at least 99.6 wt %, at least 99.7 wt %, at least 99.8 wt %, or at least 99.9 wt %, of the polypropiolactone composition comprises polypropiolactone polymers, or salts thereof, having the structure of Formula (I).
24. The method of any one of embodiments 16 to 23, wherein the polypropiolactone composition has a polydispersity index (PDI) less than 1.9, less than 1.8, less than 1.7, less than 1.6, less than 1.5, less than 1.4, less than 1.3, less than 1.2, less than 1.1, or less than 1; or between 1 and 2, between 1 and 1.9, between 1 and 1.8, between 1 and 1.7, between 1 and 1.6, or between 1 and 1.5.
25. The method of any one of embodiments 16 to 24, wherein the polypropiolactone composition has an $M_n$ less than 35,000 g/mol, less than 30,000 g/mol, less than 35,000 g/mol, less than 30,000 g/mol, less than 25,000 g/mol, less than 20,000 g/mol, less than 15,000 g/mol, less than 10,000 g/mol, less than 5,000 g/mol, less than 4,000 g/mol, less than 3,000 g/mol, less than 2,000 g/mol or less than 1,000 g/mol; or between 1,000 g/mol and 35,000 g/mol, between 1,000 g/mol and 30,000 g/mol, between 1,000 g/mol and 25,000 g/mol, between 1,000 g/mol and 20,000 g/mol, between 1,000 g/mol and 15,000 g/mol, or between 1,000 g/mol and 10,000 g/mol.
26. The method of any one of embodiments 16 to 25, wherein p is 0.
27. The method of any one of embodiments 16 to 26, wherein the salt of at least one compound of Formula (III), or a salt thereof, is combined with beta propiolactone.
28. The method of any one of embodiments 16 to 27, wherein at least one compound of Formula (III), or a salt thereof, is:

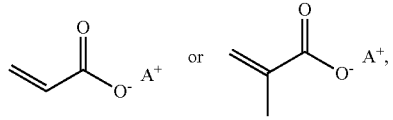

or a combination thereof, wherein $A^+$ is a Group I cation or a Group II cation.
29. The method of embodiment 28, wherein $A^+$ is $Na^+$ or $K^+$.
30. The method of embodiment 28, wherein the at least one compound of Formula (III), or a salt thereof, is:

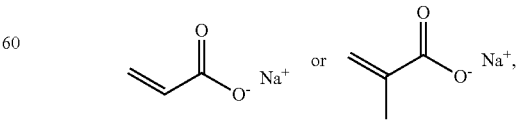

or a combination thereof.
31. A method for producing acrylic acid, comprising heating a polypropiolactone composition to produce the acrylic acid, wherein the polypropiolactone composition comprises polypropiolactone polymers, or salts thereof, independently comprising:
(a) an acrylate end group having the structure

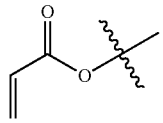

or a hydracrylate end group having the structure

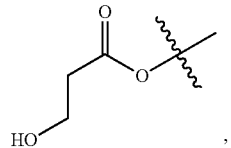 [SMILES: *OC(=O)CCO]

and
(b) a polymer chain comprising repeating units having the structure

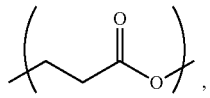

wherein the acrylate end group or the hydracrylate end group caps the alkyl terminus of the polymer chain, and
wherein:
(1) the polypropiolactone composition has an $M_n$ of less than or equal to about 40,000 g/mol; or
(2) the polypropiolactone composition has a PDI less than or equal to about 2.0; or
(3) at least 90 wt % of the polypropiolactone composition comprises polypropiolactone polymers, or salts thereof, having the acrylate end group, or
any combinations of (1)-(3).

32. The method of embodiment 31, wherein the acrylic acid is produced at a rate of at least about 500 kg/hr.
33. The method of embodiment 31 or 32, wherein at least 95 wt %, at least 96 wt %, at least 97 wt %, at least 98 wt %, at least 99 wt %, at least 99.1%, at least 99.2 wt %, at least 99.3 wt %, at least 99.4 wt %, at least 99.5 wt %, at least 99.6 wt %, at least 99.7 wt %, at least 99.8 wt %, or at least 99.9 wt %, of the polypropiolactone composition comprises polypropiolactone polymers, or salts thereof, having the acrylate end group.
34. The method of any one of embodiments 31 to 33, wherein the polypropiolactone composition has a polydispersity index (PDI) less than 1.9, less than 1.8, less than 1.7, less than 1.6, less than 1.5, less than 1.4, less than 1.3, less than 1.2, less than 1.1, or less than 1; or between 1 and 2, between 1 and 1.9, between 1 and 1.8, between 1 and 1.7, between 1 and 1.6, or between 1 and 1.5.
35. The method of any one of embodiments 31 to 34, wherein the polypropiolactone composition has an $M_n$ less than 35,000 g/mol, less than 30,000 g/mol, less than 35,000 g/mol, less than 30,000 g/mol, less than 25,000 g/mol, less than 20,000 g/mol, less than 15,000 g/mol, less than 10,000 g/mol, less than 5,000 g/mol, less than 4,000 g/mol, less than 3,000 g/mol, less than 2,000 g/mol or less than 1,000 g/mol; or between 1,000 g/mol and 35,000 g/mol, between 1,000 g/mol and 30,000 g/mol, between 1,000 g/mol and 25,000 g/mol, between 1,000 g/mol and 20,000 g/mol, between 1,000 g/mol and 15,000 g/mol, or between 1,000 g/mol and 10,000 g/mol.

36. A polypropiolactone composition, comprising polypropiolactone polymers, or salts thereof, independently comprising:
(a) an acrylate end group having the structure

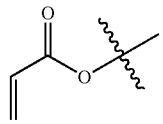 [SMILES: *OC(=O)C=C]

or a hydracrylate end group having the structure

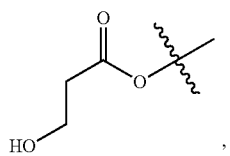

and
(b) a polymer chain comprising repeating units having the structure

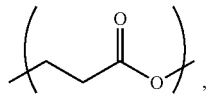

wherein the acrylate end group or the hydracrylate end group caps the alkyl terminus of the polymer chain, and
wherein:
(1) the polypropiolactone composition has an $M_n$ less than or equal to about 40,000 g/mol; or
(2) the polypropiolactone composition has a PDI less than or equal to about 2.0; or
(3) at least 90 wt % of the polypropiolactone composition comprises polypropiolactone polymers, or salts thereof, having the acrylate end group or the hydracrylate end group, or
any combinations of (1)-(3).

37. The polypropiolactone composition of embodiment 36, wherein at least 90 wt %, at least 95 wt %, at least 96 wt %, at least 97 wt %, at least 98 wt %, at least 99 wt %, at least 99.1%, at least 99.2 wt %, at least 99.3 wt %, at least 99.4 wt %, at least 99.5 wt %, at least 99.6 wt %, at least 99.7 wt %, at least 99.8 wt %, or at least 99.9 wt %, of the polypropiolactone composition comprises polypropiolactone polymers, or salts thereof, having the acrylate end group or the hydracrylate end group.
38. The polypropiolactone composition of embodiment 36 or 37, wherein the polypropiolactone composition has a polydispersity index (PDI) less than 1.9, less than 1.8, less than 1.7, less than 1.6, less than 1.5, less than 1.4, less than 1.3, less than 1.2, less than 1.1, or less than 1; or between 1 and 2, between 1 and 1.9, between 1 and 1.8, between 1 and 1.7, between 1 and 1.6, or between 1 and 1.5.
39. The polypropiolactone composition of any one of embodiments 36 to 38, wherein the polypropiolactone composition has an $M_n$ less than 35,000 g/mol, less than 30,000 g/mol, less than 35,000 g/mol, less than 30,000 g/mol, less than 25,000 g/mol, less than 20,000 g/mol, less than 15,000 g/mol, less than 10,000 g/mol, less than 5,000 g/mol, less than 4,000 g/mol, less than 3,000 g/mol, less than 2,000 g/mol or less than 1,000 g/mol; or between 1,000 g/mol and 35,000 g/mol, between 1,000 g/mol and 30,000 g/mol, between 1,000 g/mol and 25,000 g/mol, between 1,000 g/mol and 20,000 g/mol, between 1,000 g/mol and 15,000 g/mol, or between 1,000 g/mol and 10,000 g/mol.

40. The polypropiolactone composition of any one of embodiments 36 to 39, wherein the polypropiolactone polymers, or salts thereof, independently have a structure of Formula (I) or (II):

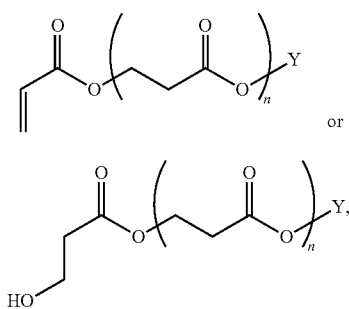

wherein:
n is an integer from 10 to 1,000; and
Y is —H or a cation.

41. A method for producing a polypropiolactone composition, comprising: combining beta propiolactone and water to produce the polypropiolactone composition,
wherein the polypropiolactone composition comprises polypropiolactone polymers, or salts thereof, independently comprising:
(a) a hydracrylate end group having the structure

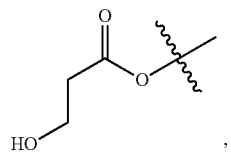 [SMILES: *OC(=O)CCO]

and
(b) a polymer chain comprising repeating units having the structure

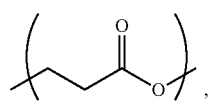

wherein the hydracrylate end group caps the alkyl terminus of the polymer chain, and
wherein:
(1) the polypropiolactone composition has an Mn less than or equal to about 40,000 g/mol; or
(2) the polypropiolactone composition has a PDI less than or equal to about 2.0; or
(3) at least 90 wt % of the polypropiolactone composition comprises polypropiolactone polymers, or salts thereof, having the hydracrylate end group, or
any combinations of (1)-(3).

42. The method of embodiment 41, wherein at least 90 wt %, at least 95 wt %, at least 96 wt %, at least 97 wt %, at least 98 wt %, at least 99 wt %, at least 99.1%, at least 99.2 wt %, at least 99.3 wt %, at least 99.4 wt %, at least 99.5 wt %, at least 99.6 wt %, at least 99.7 wt %, at least 99.8 wt %, or at least 99.9 wt %, of the polypropiolactone composition comprises polypropiolactone polymers, or salts thereof, having the hydracrylate end group.

43. The method of embodiment 41 or 42, wherein the polypropiolactone composition has a polydispersity index (PDI) less than 1.9, less than 1.8, less than 1.7, less than 1.6, less than 1.5, less than 1.4, less than 1.3, less than 1.2, less than 1.1, or less than 1; or between 1 and 2, between 1 and 1.9, between 1 and 1.8, between 1 and 1.7, between 1 and 1.6, or between 1 and 1.5.

44. The method of any one of embodiments 41 to 43, wherein the polypropiolactone composition has an $M_n$ less than 35,000 g/mol, less than 30,000 g/mol, less than 35,000 g/mol, less than 30,000 g/mol, less than 25,000 g/mol, less than 20,000 g/mol, less than 15,000 g/mol, less than 10,000 g/mol, less than 5,000 g/mol, less than 4,000 g/mol, less than 3,000 g/mol, less than 2,000 g/mol or less than 1,000 g/mol; or between 1,000 g/mol and 35,000 g/mol, between 1,000 g/mol and 30,000 g/mol, between 1,000 g/mol and 25,000 g/mol, between 1,000 g/mol and 20,000 g/mol, between 1,000 g/mol and 15,000 g/mol, or between 1,000 g/mol and 10,000 g/mol.

45. A method of producing a superabsorbent polymer, comprising:
pyrolyzing a polypropiolactone composition of any one of embodiments 36 to 40, or prepared according to the method of any one of embodiments 16 to 30, and 41 to 44, to produce acrylic acid; and
polymerizing the acrylic acid blended with sodium hydroxide in the presence of a radical initiator to produce the superabsorbent polymer.

46. A superabsorbent polymer produced according to the method of embodiment 45.

47. A reaction stream comprising polypropiolactone chains of Formula (I):

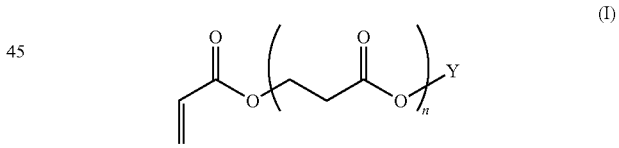

wherein:
n is an integer from 10 to about 1,000; and
Y is —H or a cation, and
wherein the reaction stream produces acrylic acid at a rate of at least about 500 kg/hr.

48. A superabsorbent polymer comprising polyacrylic acid derived from acrylic acid formed from pyrolysis of a polypropiolactone chain of Formula (I):

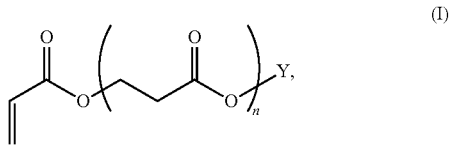

wherein:
n is an integer from 10 to about 1,000; and
Y is —H or a cation, and
wherein the superabsorbent polymer comprises less than about 1000 parts per million residual monoethylenically unsaturated monomer, and is substantially free of an aldehyde impurity or a compound derived from the oxidation of propylene.

49. The superabsorbent polymer of embodiment 48, wherein less than 100 ppm of the aldehyde impurity or the compound derived from the oxidation of propylene is present in the superabsorbent polymer.

50. The superabsorbent polymer of embodiment 48, wherein less than 10,000 ppm of the aldehyde impurity or the compound derived from the oxidation of propylene is present in the superabsorbent polymer.

51. The superabsorbent polymer of embodiment 48, wherein less than 10 ppm of the aldehyde impurity.

52. An article comprising the superabsorbent polymer of any one of embodiments 46, 48 to 41.

53. The article of embodiment 52, wherein the article is a disposable diaper.

The foregoing has been a description of certain non-limiting embodiments of the invention. Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

EXAMPLES

The following Examples are merely illustrative and are not meant to limit any aspects of the present disclosure in any way.

Example 1: Carbonylation of EO and Polymerization of BPL to Form a Polypropiolactone Chain of Formula (I)

Step 1. Under dry nitrogen, a 300 mL Parr high-pressure reactor is charged with carbonylation catalyst 1 ([(TPP)Al(THF)$_2$][Co(CO)$_4$], 286 mg, 0.3 mmol) and 85 mL of dry, deoxygenated THF.

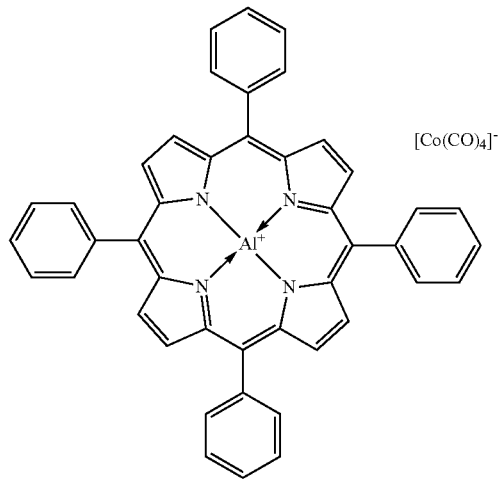

catalyst 1

The reactor is heated to 45° C., agitated at 500 rpm, and pressurized to 150 psi with CO. After the reactor temperature stabilizes, 13.5 g of EO (306 mmol) is injected under 600 psi of CO. The reaction mixture is maintained at 600 psi for 210 min after EO injection, then the CO pressure is slowly vented to ambient pressure and the BPL is carried to the next step.

Step 2. A solution of polymerization catalyst 2 is added to the reactor (PPNTFA, 1.98 g 3.0 mmol in 5 mL of methylene chloride) under nitrogen.

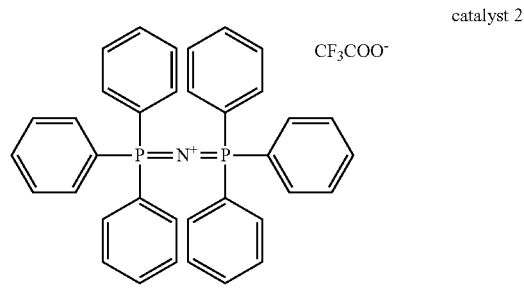

catalyst 2

Acrylic acid chain transfer agent is added to the reactor under nitrogen. The mixture is stirred in the reactor at 45° C. for 16 hours. The polymerization is quenched by addition of 33 mL of 1% HCl in MeOH. 250 mL of MeOH is then added to precipitate the polymer of formula (I). The reactor is emptied and washed with 20 mL of CHCl$_3$. The collected reaction mixture and the wash are combined, and filtered to yield a white solid. The solid is washed with 100 mL of MeOH, dissolved in 40 mL of CHCl$_3$ and re-precipitated in 300 mL of MeOH. The precipitate is filtered and washed with 200 mL of MeOH and dried in vacuum oven at 40° C. for 16 hours, to provide a Polypropiolactone chain of formula (I).

Example 2: Pyrolysis of the Polypropiolactone Chain of Formula (I)

In a 50 mL round bottom flask, 10 g of sand, 2.0 g of the Polypropiolactone chain of formula (I) from Example 1, and 8.6 mg of MEHQ (hydroquinone monomethyl ether) are combined, and the mixture stirred with a magnetic stir bar. The whole system is set under vacuum, and is closed when the pressure reaches 500 mTorr. The flask containing the polymer is then placed in a heating mantle, and heated to 210° C., while the receiving flask is immersed in dry ice/acetone bath. Acrylic acid is liberated from the polymer in the heated flask and is vacuum transferred to the receiving flask. Heating is stopped when no additional liquid is condensing in the receiving flask. At the end of the pyrolysis, a clear liquid is recovered from the receiving flask. The acrylic acid is substantially free of an aldehyde impurity or a compound that derives from the oxidation of propylene.

Example 3: Pilot Scale Production of Acrylic Acid

A first reactor proximate to a shale gas play is fed with 75 kg/hr of ethylene oxide derived from a shale gas-derived C2 product stream. The first reactor is operated at steady state conditions with a 1.5 M concentration of beta propiolactone present in the reactor volume. Additionally, 4850 L/hr of solvent containing 15 mol/hr of catalyst 1 [(TPP)Al(THF)$_2$][Co(CO)$_4$] is fed to the reactor. The reactor is maintained at a pressure of 600 psig of carbon monoxide and sized such that the feed and solvent have a residence time of at least 2.5 hours (e.g., at least 15,000 L in volume). Under these conditions, a reaction stream containing about 1740 mole/hr of beta-propiolactone is produced (125 kg/hr).

The beta-lactone stream is directed to a separation unit which separates the stream into a catalyst recycling stream containing solvent and catalyst and a beta propiolactone stream comprising beta propiolactone and solvent. The catalyst recycling stream is returned to the first reactor and the beta propiolactone stream is fed to a second reactor where it is contacted with PPN-acrylate (catalyst 2a).

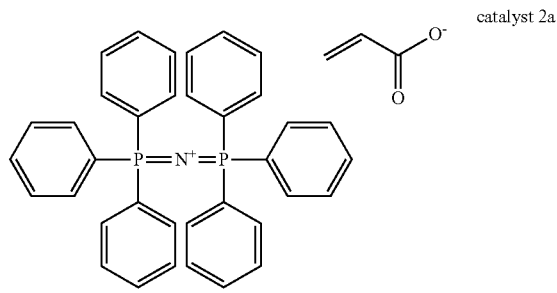

catalyst 2a

Acrylic acid chain transfer agent is added under nitrogen. The second reactor is a plug flow reactor sized such that reactants have a residence time of at least 30 minutes (e.g., 1250 L in volume) maintained at a temperature and catalyst load such that all of the lactone is consumed during the residence time. The second reactor produces approximately 1740 mole/hr of polypropiolactone chains of Formula (I) (123 kg/hr). The effluent of the plug flow reactor is treated with hydrochloric acid and methanol to precipitate the polymer. The precipitated polymer is pelletized and fed into a hopper joined to a fluidized bed reactor. The fluidized bed reactor is swept with dry nitrogen at 150° C. and fed from the hopper at a rate of 500 kg of polypropiolactone chain of Formula (I) pellets per hour. The nitrogen sweep from the fluidized bed is directed to a condenser stage which produces a stream of liquid glacial acrylic acid at a rate of approximately 480 kg/hr.

Example 4: Batch Polymerizations of Neat BPL, without Added Chain Transfer Agents Polymerizations were conducted in a Parr pressure reactor outfitted with a jacket heater and an integral in-situ IR spectrometer (ReactIR). The polymerization catalyst was charged into the reactor under a nitrogen atmosphere in a glove box to avoid oxygen and moisture contamination. It should be understood that in this reaction, the catalyst functions as an initiator in the polymerization. The reactor was then sealed, removed from the glove box and heated to a temperature (80 to 100° C.) at which time neat bPL was added in one aliquot under vigorous mixing. After an initial exotherm, the reactor was heated to maintain a temperature of 140° C. until the polymerization was complete. Results of the polymerization are shown in Table 1 below.

TABLE 1

| Exp. # | Catalyst (mmol) | bPL to initiator | Rxn time (min) | temp bPL added (° C.) | Rxn temp (° C.) | MW by NMR | TGA Onset (° C.) | Viscosity at 120° C. (poise) |
|---|---|---|---|---|---|---|---|---|
| TBAAcr | | | | | | | | |
| 117-179 | 0.039 | 9000 | 22 | 100 | 140 | 1160 | 257.3 | 11.48 |
| 117-184 | 0.030 | 11600 | 226 | 100 | 140 | 1640 | 203.8 | 35.16 |
| 117-195 | 0.024 | 14500 | 56 | 130 | 140 | 2120 | 254.7 | 7.39 |
| NaAcr | | | | | | | | |
| 117-197 | 0.189 | 1800 | 83 | 100 | 140 | 1130 | 244.0 | 41.06 |
| 117-203 | 0.183 | 1900 | 59 | 130 | 140 | 1260 | 238.5 | 47.81 |
| 117-205 | 0.183 | 1900 | 49 | 130 | 145 | 1370 | 230.5 | 77.81 |
| TBAAc | | | | | | | | |
| 117-107 | 0.042 | 8000 | 37 | 60 | 100 | 2230 | 242.2 | |
| PPNAcr | | | | | | | | |
| 11-145 | 0.035 | 10000 | 75 | 90 | 120 | 2540 | | |

TBAAcr = tetrabutylammonium acrylate
NaAcr = sodium acrylate
TBAAc = tetrabutylammonium acetate
PPNAcr = Bis(triphenylphosphine)iminium acrylate

Example 5: Batch Polymerizations of Neat BPL with Chain Transfer by Acrylic Acid (AA)

BPL polymerizations were conducted using tetrabutyl ammonium acrylate catalyst in a Parr pressure reactor according to the previous examples, except acrylic acid was added to the polymerization mixture as a chain transfer agent. Results are summarized in Table 2 below, and include experiments where the ratio of chain transfer agent to catalyst is varied from 8:1 to 478:1. Increasing ratio of acrylic acid led to PPL compositions with lower molecular weights. In each case, NMR analysis indicates essentially all of the PPL chains in the compositions have acrylate end groups.

TABLE 2

| Exp. # | Initiator (mmol) | AA added (mmol) | bPL to initiator | Rxn time (min) | temp bPL added (° C.) | Rxn temp (° C.) | MW by NMR | TGA Onset (° C.) | Viscosity at 120 C. (poise) |
|---|---|---|---|---|---|---|---|---|---|
| TBAAcr | | | | | | | | | |
| 117-162 | 0.041 | 0.33 | 9000 | 104 | 100 | 130 | 1770 | 249.4 | 19.56 |
| 117-167 | 0.040 | 1.09 | 9000 | 105 | 100 | 130 | 1680 | 243.8 | 16.04 |
| 117-195 | 0.024 | 11.48 | 9000 | 173 | 100 | 130 | 770 | 227.9 | 3.87 |

Example 6: Continuous Polymerization of THF Solutions of BPL

The following examples demonstrate the production of poly(propiolactone) from beta propiolactone in a continuous plug-flow reactor.

a) Experiment 1, BPL Polymerization with an Acetate Catalyst 500 mL of 0.100 M catalyst solution was prepared by dissolving 15.08 g of tetrabutylammonium acetate (TBA OAc, Aldrich, dried under vacuum at 90° C.) in THF (dried over active 3 Å molecular sieves) in a nitrogen glove-box.

Continuous catalytic carbonylation of ethylene oxide and nano-filtration provided a 24.7 wt % solution of beta propiolactone in THF (permeate).

Permeate and catalyst solution were fed to an 80° C. plug-flow reactor consisting of a ½"×24.75" jacketed static-mixer, with an inlet pressure transducer, and an outlet configured with a thermocouple, in-situ IR probe, and a back-pressure regulator. The permeate and catalyst solutions were fed to the reactor at rates of 1.00 and 0.100 mL/min respectively to provide a BPL:catalyst ratio of 340:1 and a reactor residence time of 23 minutes. With the reactor maintained at 100 psig and 80° C., after 70 minutes, IR spectra from the in situ probe indicated >99% conversion and product was collected in a collection bottle containing 500 mL of methanol. Product was accumulated in this manner for 198 minutes and the reactor was then rinsed with dioxane at 1.00 mL/min into a second collection vessel for further 218 minutes. Precipitate was collected by from the bottles by filtration and air dried overnight to give 52.7 g PPL as an of off-white powder (SEC: $M_n$=9610, $M_w$=16, 700; PDI=1.7; $^1$HNMR(CDCl$_3$): δ 4.34, t, 2H, δ 2.64, t, 2H, δ 6.39, dd, 0.0066H, δ 6.09, dd, 0.0066H, δ 5.82, dd, 0.0066H, δ 2.03, s, 0.026H). The ratio of the acetate resonance at δ 2.03 to the vinyl resonances in the NMR spectrum suggest approximately 43% of the PPL chains contain acrylate end groups and approximately 57% of chains contain acetate end groups.

b) Experiment 2, BPL Polymerization with an Acrylate Catalyst

This example demonstrates a continuous BPL polymerization with tetrabutylammonium acrylate catalyst. A continuous flow polymerization was performed under conditions similar to Experiment 1 above, except the polymerization catalyst source was changed to 0.049 mM tetrabutylammonium acrylate in THF fed at 0.374 g/min, the polymerization temperature was raised to 112° C., the residence time was increased to 120 minutes, and the BPL feed rate was increased to 3.364 g/min of 20 wt % BPL solution. The PPL product collected from this polymerization had an $M_n$ of 5,930 g/mol and a viscosity of 1,577 cP at 120° C. and shear of 1/s. NMR analysis indicates essentially all of the PPL chains in the composition have an acrylate end group.

What is claimed is:

1. A method for producing a polypropiolactone composition, comprising: combining beta propiolactone and at least one salt of a compound of Formula (III) to produce the polypropiolactone composition, wherein:
    the compound of Formula (III) has the structure:

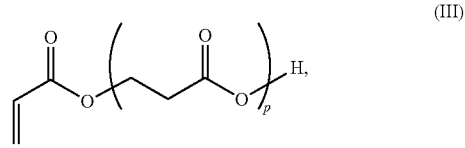

(III)

wherein p is independently an integer from 0 to 9;
    the at least one salt of the compound of Formula (III) independently comprises:
        an anion of the compound of Formula (III), and
        a cation selected from the group consisting of quaternary ammonium, protonated amine, iminium, guanidinium, phosphonium, phosphazenium, sulfonium, arsonium, and a cation of a nitrogen-containing heterocycle, or any combination thereof; and
    the polypropiolactone composition comprises polypropiolactone polymers, or salts thereof, independently comprising:
    (a) an acrylate end group having the structure

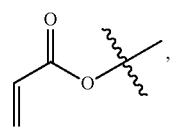 [SMILES: *OC(=O)C=C]

and (b) a polymer chain comprising repeating units having the structure

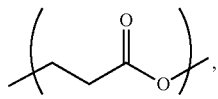

wherein the acrylate end group caps the alkyl terminus of the polymer chain, and wherein:
(1) the polypropiolactone composition has an $M_n$ less than or equal to about 40,000 g/mol; and
(2) the polypropiolactone composition has a polydispersity less than or equal to about 2.0; and
(3) at least 90 wt % of the polypropiolactone composition comprises polypropiolactone polymers, or salts thereof, having the acrylate end group.

2. The method of claim 1, wherein the polypropiolactone polymers, or salts thereof, independently have a structure of Formula (I):

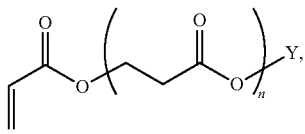 (I)

wherein:
n is an integer from 10 to 1,000; and
Y is H or a cation.

3. The method of claim 1, wherein the beta propiolactone is combined with the at least one salt of the compound of Formula (III) at a temperature greater than 50° C.

4. The method of claim 3, wherein the temperature is in the range from 140° C. to 200° C.

5. The method of claim 1, wherein at least 95 wt % of the polypropiolactone composition comprises polypropiolactone polymers, or salts thereof, having the acrylate end group.

6. The method of claim 2, wherein at least 90 wt % of the polypropiolactone composition comprises polypropiolactone polymers, or salts thereof, having the structure of Formula (I).

7. The method of claim 2, wherein the polypropiolactone composition has a polydispersity index (PDI) less than 1.7.

8. The method of claim 1, wherein p is 0.

9. A method of producing a superabsorbent polymer, comprising:
converting a polypropiolactone composition of claim 1 to produce acrylic acid, and
polymerizing the acrylic acid blended with sodium hydroxide in the presence of a radical initiator to produce the superabsorbent polymer.

10. A superabsorbent polymer produced according to the method of claim 9.

11. The method of claim 1, wherein the combining of beta propiolactone and the at least one salt of the compound of Formula (III) produces a chain transfer agent, wherein the chain transfer agent is at least one salt independently comprising an acrylate end group having the structure

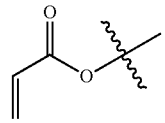 [SMILES: *OC(=O)C=C]

wherein the acrylate end group caps the alkyl terminus of the polymer chain.

12. The method of claim 11, wherein the chain transfer agent is at least one salt independently further comprising: a chain comprising one or more units having the structure

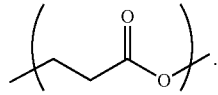

13. The method of claim 8, wherein the at least one salt of the compound of Formula (III) comprises a cation selected from the group consisting of ammonium, protonated amine, and iminium.

14. The method of claim 13, wherein the ratio of the beta propiolactone to the at least one salt of the compound of Formula (III) is between 1:9,000 and 1:14,500.

15. The method of claim 1, wherein the beta propiolactone and the at least one salt of the compound of Formula (III) are further combined with a compound of Formula (III).

* * * * *